United States Patent
Leung et al.

(10) Patent No.: US 6,274,363 B1
(45) Date of Patent: *Aug. 14, 2001

(54) PHOSPHATIDYLCHOLINE PHOSPHOLIPASE D

(75) Inventors: David W. Leung, Mercer Island; Christopher K. Tompkins, Bothell, both of WA (US)

(73) Assignee: Cell Therapeutics, Inc., Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/107,149

(22) Filed: Jun. 30, 1998

Related U.S. Application Data

(63) Continuation-in-part of application No. 08/768,147, filed on Dec. 17, 1996, now Pat. No. 5,859,222.
(60) Provisional application No. 60/008,768, filed on Dec. 15, 1995.

(51) Int. Cl.$^7$ .............. C12N 9/20; C12N 1/20; C12N 15/00; C07H 21/04
(52) U.S. Cl. .......... 435/198; 435/252.3; 435/320.1; 536/23.2; 536/23.5
(58) Field of Search ............... 435/198, 252.3, 435/320.1; 536/23.2, 23.5; 530/350

(56) References Cited

U.S. PATENT DOCUMENTS

| | | | |
|---|---|---|---|
| 5,342,764 | 8/1994 | Johnson et al. | 435/69.1 |
| 5,859,222 | * 1/1999 | Leung et al. | 536/23.2 |
| 6,043,073 | * 3/2000 | Frohman et al. | 435/198 |

FOREIGN PATENT DOCUMENTS

98/10076   3/1998   (WO) .

OTHER PUBLICATIONS

Kodaki et al. J. Biol. Chem. 272 (17): 11408–11413 (Apr. 27, 1997).*

Lopez et al. J. Biol. Chem. (May 22, 1998). 273 (21) : 12846–52.*

Sequence comparison AF035483 and SEQ ID NO : 16, May 22, 1998.*

Barbas et al., "Methods: A Companion to Methods in Enzymology", vol. 2 No. 2, *Combinatorial Immunoglobulin Libraries on the Surface of Phage (Phabs): Rapid Selection of Antigen–Specific Fabs*, pp. 119–124, (1991).

Brown et al., "Journal of Biological Chemistry", vol. 270, No. 25, *Partial Purification and Characterization of Arf––sensitive Phospholipase D from Porcine Brain*, pp. 14935–14943, (1995).

Ella et al., "Analytical Biochemistry", vol. 218, *A Fluorescent Assay for Agonist–Activated Phospholipase D in Mammalian Cell Extracts*, pp. 136–142, (1994).

Ella et al., "Biochem. J.", vol. 314, *Characterization of Saccharomyces cerevisiae dificient in expression of phospholipase D*, pp. 15–19, (1996).

Exton, "Biochimica et Biophysica Acta", vol. 1212, *Phosphatidylcholine breakdown and signal transduction*, pp. 26–42, (1994).

Hammond et al., "Journal of Biological Chemistry", vol. 270 No. 50, *Human ADP–ribosylation Factor–activated Phospholipase D Defines a New and Highly Conserved Gene Family*, pp. 29640–29643, (1995).

Honigberg et al., "Genetics", vol. 130, *Commitment to Meiosis in Saccharomyces Cerevisiae: Involvement of the SPO14 Gene*, pp. 703–716, (1992).

Kiss, "Chemistry and Physics of Lipids", vol. 80, *Regulation of phospholipase D by protein kinase C*, pp. 81–102, (1996).

Kozak, "Critical Reviews in Biochemistry and Molecular Biology", vol. 27(4,5), *A Consideration of Alternative Models for the Initiation of Translation in Eukaryotes*, pp. 385–402, (1992).

Redina et al.; "Genomic Analysis of Murine Phospholipase D1 and Comparison to Phospholipase D2 Reveals An Unusual Difference in Gene Size"; Gene 22; 1998; pp. 53–60.

AACR Abstract; "Overexpression of Phospholipase D in Human Breast Cancer Tissues"; 1999; 1 sheet.

Uetsuki et al., "Journal of Biological Chemistry", vol. 264 No. 10, *Isolation and Characterization of the Human Chromosomal Gene for Polypeptide Chain Elongation Factor–1α*, pp. 5791–578, (1989).

Vinggaard et al., "Biochemica et Biophysica Acta", vol. 1258, *Characterization and partial purification of phospholipase D from human placenta*, pp. 169–176, (1995).

Wang et al., "Journal of Biological Chemistry", vol. 269 No. 32, *Cloning and Expression of Phosphatidylcholine–hydrolyzing Phospholipase D from Ricinus communis L*, pp. 20312–20317, (1994).

Winter et al., "Annu. Rev. Immunol.", vol. 12, *Making Antibodies by Phase Display Technology*, pp. 433–455, (1994).

Lavallie et al., "Journal of Biological Chemistry", vol. 268 No. 31, *Cloning and Functional Expression of a cDNA Encoding the Catalytic Subunit of Bovine Enterokinase*, pp. 23311–23317, (1993).

(List continued on next page.)

Primary Examiner—Ponnathapu Achutamurthy
Assistant Examiner—Tekchand Saidha
(74) Attorney, Agent, or Firm—Foley & Lardner

(57) ABSTRACT

Three new isoforms of phosphatidylcholine phospholipase D, hPLD2.1, hPLD2.2 and hPLD1.5, can be produced recombinantly and are useful for screening compounds, as drug candidates, for an ability to modify PCPLD activity.

10 Claims, 3 Drawing Sheets

OTHER PUBLICATIONS

Leung et al., "Proc. Natl. Acad. Sci.", vol. 92, *CT–2576, an inhibitor of phospholipid signaling, suppresses constitutive and induced expression of human immunodeficiecy virus*, pp. 4813–4817, (1995).

Liscovitch et al., "Chemistry and Physics and Lipids", vol. 80, *Enzymology of mammalian phospholipases D: in vitro studies*, pp. 37–44, (1996).

Okamura et al., Journal of Biological Chemistry, vol. 269 No. 49, *Purification and Characterization of Phosphatidylcholine Phospholipase D from Pig Lung*, pp. 31207–31213, (1994).

Rice et al., "Proc. Natl. Acad. Sci. USA", vol. 91, *Protection from endotoxic shock in mice by pharmacologic inhibition of phosphatidic Acid*, pp. 3857–3861, (1994).

Rose et al., "Proc. Natl. Acad. Sci. USA", vol. 92, *Phospholipase D signaling is essential for meiosis*, pp. 12151–1215, (1995).

Saito et al., "Archives of Biochemistry and Biophysics", vol. 169, *Phosphatidohydrolase Activity in a Solubilized Preparation From Rat Brain Particulate Fraction*, pp. 318–323, (1975).

Singer et al., "Exp. Opin. Invest. Drugs", vol. 3 No. 6, *Inhibitors of Intracellular Phosphatidic Acid Production: Novel Therapeutics with Broad Clinical Applications*, pp. 631–643, (1994).

Ueki et al., "Plan Cell Physiol.", vol. 36 No. 5, *Purification and Characterization of Phospholipase D (PLD) from Rice (Oryza sativa L.) and Cloning of cDNA for PLD from Rice and Maize (Zea mays L.)*, pp. 903–914, (1995).

\* cited by examiner

SEQUENCE LISTING

<160> NUMBER OF SEQ ID NOS: 25

<210> SEQ ID NO 1
<211> LENGTH: 3425
<212> TYPE: DNA
<213> ORGANISM: Homo sapiens
<220> FEATURE:
<221> NAME/KEY: CDS
<222> LOCATION: (64)..(2862)

<400> SEQUENCE: 1

```
tgcagctccg gtctgctctc ttggctcggg aacccccgcg ggcgctggct ccgtctgcca      60 ggg atg acg gcg acc cct gag agc ctc ttc ccc act ggg gac gaa ctg     108
    Met Thr Ala Thr Pro Glu Ser Leu Phe Pro Thr Gly Asp Glu Leu
    1               5                   10                  15
```

-continued

| | |
|---|---|
| gac tcc agc cag ctc cag atg gag tcc gat gag gtg gac acc ctg aag<br>Asp Ser Ser Gln Leu Gln Met Glu Ser Asp Glu Val Asp Thr Leu Lys<br>              20                        25                      30 | 156 |
| gag gga gag gac cca gcc gac cgg atg cac ccg ttt ctg gca atc tat<br>Glu Gly Glu Asp Pro Ala Asp Arg Met His Pro Phe Leu Ala Ile Tyr<br>              35                        40                        45 | 204 |
| gag ctt cag tct ctg aaa gtg cac ccc ttg gtg ttc gca cct ggg gtc<br>Glu Leu Gln Ser Leu Lys Val His Pro Leu Val Phe Ala Pro Gly Val<br>              50                        55                        60 | 252 |
| cct gtc aca gcc cag gtg gtg ggc acc gaa aga tat acc agc gga tcc<br>Pro Val Thr Ala Gln Val Val Gly Thr Glu Arg Tyr Thr Ser Gly Ser<br>65                        70                        75 | 300 |
| aag gtg gga acc tgc act ctg tat tct gtc cgc ttg act cac ggc gac<br>Lys Val Gly Thr Cys Thr Leu Tyr Ser Val Arg Leu Thr His Gly Asp<br>80                        85                        90                        95 | 348 |
| ttt tcc tgg aca acc aag aag aaa tac cgt cat ttt cag gag ctg cat<br>Phe Ser Trp Thr Thr Lys Lys Lys Tyr Arg His Phe Gln Glu Leu His<br>                    100                        105                    110 | 396 |
| cgg gac ctc ctg aga cac aaa gtc ttg atg agt ctg ctc cct ctg gct<br>Arg Asp Leu Leu Arg His Lys Val Leu Met Ser Leu Leu Pro Leu Ala<br>              115                        120                    125 | 444 |
| cga ttt gcc gtt gcc tat tct cca gcc cga gat gca ggc aac aga gag<br>Arg Phe Ala Val Ala Tyr Ser Pro Ala Arg Asp Ala Gly Asn Arg Glu<br>130                        135                        140 | 492 |
| atg ccc tct cta ccc cgg gca ggt cct gag ggc tcc acc aga cat gca<br>Met Pro Ser Leu Pro Arg Ala Gly Pro Glu Gly Ser Thr Arg His Ala<br>145                        150                        155 | 540 |
| gcc agc aaa cag aaa tac ctg gag aat tac ctc aac cgt ctc ttg acc<br>Ala Ser Lys Gln Lys Tyr Leu Glu Asn Tyr Leu Asn Arg Leu Leu Thr<br>160                        165                        170                    175 | 588 |
| atg tct ttc tat cgc aac tac cat gcc atg aca gag ttc ctg gaa gtc<br>Met Ser Phe Tyr Arg Asn Tyr His Ala Met Thr Glu Phe Leu Glu Val<br>                    180                        185                    190 | 636 |
| agt cag ctg tcc ttt atc ccg gaa ttg ggc cgc aaa gga ctg gag ggg<br>Ser Gln Leu Ser Phe Ile Pro Glu Leu Gly Arg Lys Gly Leu Glu Gly<br>              195                        200                    205 | 684 |
| atg atc cgg aag cgc tca ggt ggc cac cgt gtt tct ggc ctc acc tgc<br>Met Ile Arg Lys Arg Ser Gly Gly His Arg Val Ser Gly Leu Thr Cys<br>              210                        215                    220 | 732 |
| tgt ggc cga gac caa gtt tgt tat cgc tgg tcc aag agg tgg ctg gtg<br>Cys Gly Arg Asp Gln Val Cys Tyr Arg Trp Ser Lys Arg Trp Leu Val<br>225                        230                        235 | 780 |
| gtg aag gac tcc ttc ctg ctc tac atg tgc ctc gag aca ggt gcc atc<br>Val Lys Asp Ser Phe Leu Leu Tyr Met Cys Leu Glu Thr Gly Ala Ile<br>240                        245                        250                    255 | 828 |
| tca ttt gtt cag ctc ttt gac cct ggc ttt gag gtg caa gtg ggg aaa<br>Ser Phe Val Gln Leu Phe Asp Pro Gly Phe Glu Val Gln Val Gly Lys<br>                    260                        265                    270 | 876 |
| agg agc acg gag gca cgg cac ggc gtg cgg atc gat acc tcc cac agg<br>Arg Ser Thr Glu Ala Arg His Gly Val Arg Ile Asp Thr Ser His Arg<br>              275                        280                    285 | 924 |
| tcc ttg att ctc aag tgc agc agc tac cgg cag gca cgg tgg tgg gcc<br>Ser Leu Ile Leu Lys Cys Ser Ser Tyr Arg Gln Ala Arg Trp Trp Ala<br>              290                        295                    300 | 972 |
| caa gag atc act gag ctg gca cag ggc cca gga aga gac ttc cta cag<br>Gln Glu Ile Thr Glu Leu Ala Gln Gly Pro Gly Arg Asp Phe Leu Gln<br>305                        310                        315 | 1020 |
| ctg cac cgg cat gac agc tac gcc cca ccc cgg cct ggg acc ttg gcc<br>Leu His Arg His Asp Ser Tyr Ala Pro Pro Arg Pro Gly Thr Leu Ala<br>320                        325                        330                    335 | 1068 |

```
cgg tgg ttt gtg aat ggg gca ggt tac ttt gct gct gtg gca gat gcc    1116
Arg Trp Phe Val Asn Gly Ala Gly Tyr Phe Ala Ala Val Ala Asp Ala
                340                 345                 350 atc ctt cga gct caa gag gag att ttc atc aca gac tgg tgg ttg agt    1164
Ile Leu Arg Ala Gln Glu Glu Ile Phe Ile Thr Asp Trp Trp Leu Ser
            355                 360                 365 cct gag gtt tac ctg aag cgt ccg gcc cat tca gat gac tgg aga ctg    1212
Pro Glu Val Tyr Leu Lys Arg Pro Ala His Ser Asp Asp Trp Arg Leu
        370                 375                 380 gac att atg ctc aag agg aag gcg gag gag ggt gtc cgt gtg tct att    1260
Asp Ile Met Leu Lys Arg Lys Ala Glu Glu Gly Val Arg Val Ser Ile
    385                 390                 395 ctg ctg ttt aaa gaa gtg gaa ttg gcc ttg ggc atc aac agt ggc tat    1308
Leu Leu Phe Lys Glu Val Glu Leu Ala Leu Gly Ile Asn Ser Gly Tyr
400                 405                 410                 415 agc aag aag gcg ctg atg ctg ctc cac ccc aac ata aag gtg atg cgt    1356
Ser Lys Lys Ala Leu Met Leu Leu His Pro Asn Ile Lys Val Met Arg
                420                 425                 430 cac cca gac caa gtg acg ttg tgg gcc cat cat gag aag ctc ctg gtg    1404
His Pro Asp Gln Val Thr Leu Trp Ala His His Glu Lys Leu Leu Val
            435                 440                 445 gtg gac caa gtg gta gca ttc ctg ggg gga ctg gac ctt gcc tat ggc    1452
Val Asp Gln Val Val Ala Phe Leu Gly Gly Leu Asp Leu Ala Tyr Gly
        450                 455                 460 cgc tgg gat gac ctg cac tac cga ctg act gac ctt gga gac tcc tct    1500
Arg Trp Asp Asp Leu His Tyr Arg Leu Thr Asp Leu Gly Asp Ser Ser
    465                 470                 475 gaa tca gct gcc tcc cag cct ccc acc ccg cgc cca gac tca cca gcc    1548
Glu Ser Ala Ala Ser Gln Pro Pro Thr Pro Arg Pro Asp Ser Pro Ala
480                 485                 490                 495 acc cca gac ctc tct cac aac caa ttc ttc tgg ctg ggc aag gac tac    1596
Thr Pro Asp Leu Ser His Asn Gln Phe Phe Trp Leu Gly Lys Asp Tyr
                500                 505                 510 agc aat ctt atc acc aat gac tgg gtg cag ctg gac cgg cct ttc gaa    1644
Ser Asn Leu Ile Thr Asn Asp Trp Val Gln Leu Asp Arg Pro Phe Glu
            515                 520                 525 gat ttc att gac agg gag acg acc cct cgg atg cca tgg cgg gac gtt    1692
Asp Phe Ile Asp Arg Glu Thr Thr Pro Arg Met Pro Trp Arg Asp Val
        530                 535                 540 ggg gtg gtc gtc cat ggc cta ccg gcc cgg gac ctt gcc cgg cac ttc    1740
Gly Val Val Val His Gly Leu Pro Ala Arg Asp Leu Ala Arg His Phe
    545                 550                 555 atc cag cgc tgg aac ttc acc aag acc acc aag gcc aag tac aag act    1788
Ile Gln Arg Trp Asn Phe Thr Lys Thr Thr Lys Ala Lys Tyr Lys Thr
560                 565                 570                 575 ccc aca tac ccc tac ctg ctt ccc aag tct acc agc acg gcc aat cag    1836
Pro Thr Tyr Pro Tyr Leu Leu Pro Lys Ser Thr Ser Thr Ala Asn Gln
                580                 585                 590 ctc ccc ttc aca ctt cca gga ggg cag tgc acc acc gta cag gtc ttg    1884
Leu Pro Phe Thr Leu Pro Gly Gly Gln Cys Thr Thr Val Gln Val Leu
            595                 600                 605 cga tca gtg gac cgc tgg tca gca ggg act ctg gag aac tcc atc ctc    1932
Arg Ser Val Asp Arg Trp Ser Ala Gly Thr Leu Glu Asn Ser Ile Leu
        610                 615                 620 aat gcc tac ctg cac acc atc agg ggg agc cag cac ttc ctc tac att    1980
Asn Ala Tyr Leu His Thr Ile Arg Gly Ser Gln His Phe Leu Tyr Ile
    625                 630                 635 gag aat cag ttc ttc att agc tgc tca gat ggg cgg acg gtt ctg aac    2028
Glu Asn Gln Phe Phe Ile Ser Cys Ser Asp Gly Arg Thr Val Leu Asn
```

-continued

```
           640                 645                 650                 655
aag gtg ggc gat gag att gtg gac aga atc ctg aag gcc cac aaa cag       2076
Lys Val Gly Asp Glu Ile Val Asp Arg Ile Leu Lys Ala His Lys Gln
                    660                 665                 670 ggg tgg tgt tac cga gtc tac gtg ctt ttg ccc tta ctc cct ggc ttc       2124
Gly Trp Cys Tyr Arg Val Tyr Val Leu Leu Pro Leu Leu Pro Gly Phe
                675                 680                 685 gag ggt gac atc tcc acg ggc ggt ggc aag tcc atc cag gcc att ctg       2172
Glu Gly Asp Ile Ser Thr Gly Gly Gly Lys Ser Ile Gln Ala Ile Leu
            690                 695                 700 cac ttt act tac agg acc ctg tgt cgt ggg gag tat tca atc ctg cat       2220
His Phe Thr Tyr Arg Thr Leu Cys Arg Gly Glu Tyr Ser Ile Leu His
        705                 710                 715 cgc ctt aaa gca gcc atg ggg aca gca tgg cgg gac tat att tcc atc       2268
Arg Leu Lys Ala Ala Met Gly Thr Ala Trp Arg Asp Tyr Ile Ser Ile
720                 725                 730                 735 tgc ggg ctt cgt aca cac gga gag ctg ggc ggg cac ccc gtc tcg gag       2316
Cys Gly Leu Arg Thr His Gly Glu Leu Gly Gly His Pro Val Ser Glu
                    740                 745                 750 ctc atc tac atc cac agc aag gtg ctc atc gca gat gac cgg aca gtc       2364
Leu Ile Tyr Ile His Ser Lys Val Leu Ile Ala Asp Asp Arg Thr Val
                755                 760                 765 atc att gat tct gca aac atc aat gac cgg agc ttg ctg ggg aag cgg       2412
Ile Ile Asp Ser Ala Asn Ile Asn Asp Arg Ser Leu Leu Gly Lys Arg
            770                 775                 780 gac agt gag ctg gcc gtg cta atc gag gac aca gag acg gaa cca tcc       2460
Asp Ser Glu Leu Ala Val Leu Ile Glu Asp Thr Glu Thr Glu Pro Ser
        785                 790                 795 ctc atg aat ggg gca gag tat cag gcg ggc agg ttt gcc ttg agt ctg       2508
Leu Met Asn Gly Ala Glu Tyr Gln Ala Gly Arg Phe Ala Leu Ser Leu
800                 805                 810                 815 cgg aag cac tgc ttc agt gtg att ctt gga gca aat acc cgg cca gac       2556
Arg Lys His Cys Phe Ser Val Ile Leu Gly Ala Asn Thr Arg Pro Asp
                    820                 825                 830 ttg gat ctc cga gac ccc atc tgt gat gac ttc ttc cag ttg tgg caa       2604
Leu Asp Leu Arg Asp Pro Ile Cys Asp Asp Phe Phe Gln Leu Trp Gln
                835                 840                 845 gac atg gct gag agc aac gcc aat atc tat gag cag atc ttc cgc tgc       2652
Asp Met Ala Glu Ser Asn Ala Asn Ile Tyr Glu Gln Ile Phe Arg Cys
            850                 855                 860 ctg cca tcc aat gcc acg cgt tcc ctg cgg act ctc cgg gag tac gtg       2700
Leu Pro Ser Asn Ala Thr Arg Ser Leu Arg Thr Leu Arg Glu Tyr Val
        865                 870                 875 gcc gtg gag ccc ttg gcc acg gtc agt ccc ccc ttg gct cgg tct gag       2748
Ala Val Glu Pro Leu Ala Thr Val Ser Pro Pro Leu Ala Arg Ser Glu
880                 885                 890                 895 ctc acc cag gtc cag ggc cac ctg gtc cac ttc ccc ctc aag ttc cta       2796
Leu Thr Gln Val Gln Gly His Leu Val His Phe Pro Leu Lys Phe Leu
                    900                 905                 910 gag gat gag tct ttg ctg ccc ccg ctg ggt agc aag gag ggc aag atc       2844
Glu Asp Glu Ser Leu Leu Pro Pro Leu Gly Ser Lys Glu Gly Lys Ile
                915                 920                 925 ccc cta gaa gtg tgg aca tagttgaggc cccgtcagg gagaggtcac              2892
Pro Leu Glu Val Trp Thr
            930 cagctgctgt gccccaccac gtctggctcc ctgcccctta accccaagga ctgagggcag    2952 tgcccttga gatctgggga ggcaggcatt cctgaaggga actagaggtg ttacagagga     3012 cccttacgtg agaaatagct gaaaagggca ctcccaaccc tgggctgggg aggaggagag    3072
```

-continued

```
agtcccagag ctcatccccc ctgctgccca gtgcaaacca cttctccatg ctgcaaagga    3132
gaagcacagc tcctgccagg gtgagcaggg tcaagcctct tattccagga gaagggggct    3192 ctgcccagg  ccctactacc cattgttccc ttcctcttcc tgcccttgaa cccctcccct    3252
gtcccagggc cctcccagcc cattgctgcc aaggtggagg gaaggataaa gccacttctg    3312
gcttcagccc ccaccagggg aaggaaggag ggcacattaa ctccctccac cagcctgctg    3372
acagacacta actttgtatc cgttcaataa gcatttcata aaaaaaaaaa aaa           3425
```

<210> SEQ ID NO 2
<211> LENGTH: 933
<212> TYPE: PRT
<213> ORGANISM: Homo sapiens

<400> SEQUENCE: 2

```
Met Thr Ala Thr Pro Glu Ser Leu Phe Pro Thr Gly Asp Glu Leu Asp
 1               5                  10                  15

Ser Ser Gln Leu Gln Met Glu Ser Asp Glu Val Asp Thr Leu Lys Glu
            20                  25                  30

Gly Glu Asp Pro Ala Asp Arg Met His Pro Phe Leu Ala Ile Tyr Glu
        35                  40                  45

Leu Gln Ser Leu Lys Val His Pro Leu Val Phe Ala Pro Gly Val Pro
    50                  55                  60

Val Thr Ala Gln Val Val Gly Thr Glu Arg Tyr Thr Ser Gly Ser Lys
65                  70                  75                  80

Val Gly Thr Cys Thr Leu Tyr Ser Val Arg Leu Thr His Gly Asp Phe
                85                  90                  95

Ser Trp Thr Thr Lys Lys Tyr Arg His Phe Gln Glu Leu His Arg
            100                 105                 110

Asp Leu Leu Arg His Lys Val Leu Met Ser Leu Leu Pro Leu Ala Arg
        115                 120                 125

Phe Ala Val Ala Tyr Ser Pro Ala Arg Asp Ala Gly Asn Arg Glu Met
    130                 135                 140

Pro Ser Leu Pro Arg Ala Gly Pro Glu Gly Ser Thr Arg His Ala Ala
145                 150                 155                 160

Ser Lys Gln Lys Tyr Leu Glu Asn Tyr Leu Asn Arg Leu Leu Thr Met
                165                 170                 175

Ser Phe Tyr Arg Asn Tyr His Ala Met Thr Glu Phe Leu Glu Val Ser
            180                 185                 190

Gln Leu Ser Phe Ile Pro Glu Leu Gly Arg Lys Gly Leu Glu Gly Met
        195                 200                 205

Ile Arg Lys Arg Ser Gly Gly His Arg Val Ser Gly Leu Thr Cys Cys
    210                 215                 220

Gly Arg Asp Gln Val Cys Tyr Arg Trp Ser Lys Arg Trp Leu Val Val
225                 230                 235                 240

Lys Asp Ser Phe Leu Leu Tyr Met Cys Leu Glu Thr Gly Ala Ile Ser
                245                 250                 255

Phe Val Gln Leu Phe Asp Pro Gly Phe Glu Val Gln Val Gly Lys Arg
            260                 265                 270

Ser Thr Glu Ala Arg His Gly Val Arg Ile Asp Thr Ser His Arg Ser
        275                 280                 285

Leu Ile Leu Lys Cys Ser Ser Tyr Arg Gln Ala Arg Trp Trp Ala Gln
    290                 295                 300

Glu Ile Thr Glu Leu Ala Gln Gly Pro Gly Arg Asp Phe Leu Gln Leu
```

-continued

```
305                 310                 315                 320

His Arg His Asp Ser Tyr Ala Pro Pro Arg Pro Gly Thr Leu Ala Arg
                325                 330                 335

Trp Phe Val Asn Gly Ala Gly Tyr Phe Ala Ala Val Ala Asp Ala Ile
                340                 345                 350

Leu Arg Ala Gln Glu Glu Ile Phe Ile Thr Asp Trp Trp Leu Ser Pro
                355                 360                 365

Glu Val Tyr Leu Lys Arg Pro Ala His Ser Asp Asp Trp Arg Leu Asp
                370                 375                 380

Ile Met Leu Lys Arg Lys Ala Glu Glu Gly Val Arg Val Ser Ile Leu
385                 390                 395                 400

Leu Phe Lys Glu Val Glu Leu Ala Leu Gly Ile Asn Ser Gly Tyr Ser
                405                 410                 415

Lys Lys Ala Leu Met Leu Leu His Pro Asn Ile Lys Val Met Arg His
                420                 425                 430

Pro Asp Gln Val Thr Leu Trp Ala His His Glu Lys Leu Leu Val Val
                435                 440                 445

Asp Gln Val Val Ala Phe Leu Gly Gly Leu Asp Leu Ala Tyr Gly Arg
                450                 455                 460

Trp Asp Asp Leu His Tyr Arg Leu Thr Asp Leu Gly Asp Ser Ser Glu
465                 470                 475                 480

Ser Ala Ala Ser Gln Pro Pro Thr Pro Arg Pro Asp Ser Pro Ala Thr
                485                 490                 495

Pro Asp Leu Ser His Asn Gln Phe Phe Trp Leu Gly Lys Asp Tyr Ser
                500                 505                 510

Asn Leu Ile Thr Asn Asp Trp Val Gln Leu Asp Arg Pro Phe Glu Asp
                515                 520                 525

Phe Ile Asp Arg Glu Thr Thr Pro Arg Met Pro Trp Arg Asp Val Gly
                530                 535                 540

Val Val Val His Gly Leu Pro Ala Arg Asp Leu Ala Arg His Phe Ile
545                 550                 555                 560

Gln Arg Trp Asn Phe Thr Lys Thr Thr Lys Ala Lys Tyr Lys Thr Pro
                565                 570                 575

Thr Tyr Pro Tyr Leu Leu Pro Lys Ser Thr Ser Thr Ala Asn Gln Leu
                580                 585                 590

Pro Phe Thr Leu Pro Gly Gly Gln Cys Thr Thr Val Gln Val Leu Arg
                595                 600                 605

Ser Val Asp Arg Trp Ser Ala Gly Thr Leu Glu Asn Ser Ile Leu Asn
                610                 615                 620

Ala Tyr Leu His Thr Ile Arg Gly Ser Gln His Phe Leu Tyr Ile Glu
625                 630                 635                 640

Asn Gln Phe Phe Ile Ser Cys Ser Asp Gly Arg Thr Val Leu Asn Lys
                645                 650                 655

Val Gly Asp Glu Ile Val Asp Arg Ile Leu Lys Ala His Lys Gln Gly
                660                 665                 670

Trp Cys Tyr Arg Val Tyr Val Leu Leu Pro Leu Leu Pro Gly Phe Glu
                675                 680                 685

Gly Asp Ile Ser Thr Gly Gly Gly Lys Ser Ile Gln Ala Ile Leu His
                690                 695                 700

Phe Thr Tyr Arg Thr Leu Cys Arg Gly Glu Tyr Ser Ile Leu His Arg
705                 710                 715                 720

Leu Lys Ala Ala Met Gly Thr Ala Trp Arg Asp Tyr Ile Ser Ile Cys
                725                 730                 735
```

```
Gly Leu Arg Thr His Gly Glu Leu Gly Gly His Pro Val Ser Glu Leu
            740                 745                 750

Ile Tyr Ile His Ser Lys Val Leu Ile Ala Asp Asp Arg Thr Val Ile
            755                 760                 765

Ile Asp Ser Ala Asn Ile Asn Asp Arg Ser Leu Leu Gly Lys Arg Asp
        770                 775                 780

Ser Glu Leu Ala Val Leu Ile Glu Asp Thr Glu Thr Glu Pro Ser Leu
785                 790                 795                 800

Met Asn Gly Ala Glu Tyr Gln Ala Gly Arg Phe Ala Leu Ser Leu Arg
                805                 810                 815

Lys His Cys Phe Ser Val Ile Leu Gly Ala Asn Thr Arg Pro Asp Leu
            820                 825                 830

Asp Leu Arg Asp Pro Ile Cys Asp Asp Phe Phe Gln Leu Trp Gln Asp
        835                 840                 845

Met Ala Glu Ser Asn Ala Asn Ile Tyr Glu Gln Ile Phe Arg Cys Leu
    850                 855                 860

Pro Ser Asn Ala Thr Arg Ser Leu Arg Thr Leu Arg Glu Tyr Val Ala
865                 870                 875                 880

Val Glu Pro Leu Ala Thr Val Ser Pro Pro Leu Ala Arg Ser Glu Leu
                885                 890                 895

Thr Gln Val Gln Gly His Leu Val His Phe Pro Leu Lys Phe Leu Glu
            900                 905                 910

Asp Glu Ser Leu Leu Pro Pro Leu Gly Ser Lys Glu Gly Lys Ile Pro
        915                 920                 925

Leu Glu Val Trp Thr
        930

<210> SEQ ID NO 3
<211> LENGTH: 1074
<212> TYPE: PRT
<213> ORGANISM: Homo sapiens

<400> SEQUENCE: 3

Met Ser Leu Lys Asn Glu Pro Arg Val Asn Thr Ser Ala Leu Gln Lys
  1               5                  10                  15

Ile Ala Ala Asp Met Ser Asn Ile Ile Glu Asn Leu Asp Thr Arg Glu
                20                  25                  30

Leu His Phe Glu Gly Glu Glu Val Asp Tyr Asp Val Ser Pro Ser Asp
            35                  40                  45

Pro Lys Ile Gln Glu Val Tyr Ile Pro Phe Ser Ala Ile Tyr Asn Thr
        50                  55                  60

Gln Gly Phe Lys Glu Pro Asn Ile Gln Thr Tyr Leu Ser Gly Cys Pro
 65                  70                  75                  80

Ile Lys Ala Gln Val Leu Glu Val Glu Arg Phe Thr Ser Thr Thr Arg
                85                  90                  95

Val Pro Ser Ile Asn Leu Tyr Thr Ile Glu Leu Thr His Gly Glu Phe
            100                 105                 110

Lys Trp Gln Val Lys Arg Lys Phe Lys His Phe Gln Glu Phe His Arg
        115                 120                 125

Glu Leu Leu Lys Tyr Lys Ala Phe Ile Arg Ile Pro Ile Pro Thr Arg
    130                 135                 140

Arg His Thr Phe Arg Arg Gln Asn Val Arg Glu Glu Pro Arg Glu Met
145                 150                 155                 160

Pro Ser Leu Pro Arg Ser Ser Glu Asn Met Ile Arg Glu Glu Gln Phe
```

```
                165                 170                 175
Leu Gly Arg Arg Lys Gln Leu Glu Asp Tyr Leu Thr Lys Ile Leu Lys
                180                 185                 190
Met Pro Met Tyr Arg Asn Tyr His Ala Thr Thr Glu Phe Leu Asp Ile
            195                 200                 205
Ser Gln Leu Ser Phe Ile His Asp Leu Gly Pro Lys Gly Ile Glu Gly
        210                 215                 220
Met Ile Met Lys Arg Ser Gly Gly His Arg Ile Pro Gly Leu Asn Cys
225                 230                 235                 240
Cys Gly Gln Gly Arg Ala Cys Tyr Arg Trp Ser Lys Arg Trp Leu Ile
                245                 250                 255
Val Lys Asp Ser Phe Leu Leu Tyr Met Lys Pro Asp Ser Gly Ala Ile
            260                 265                 270
Ala Phe Val Leu Leu Val Asp Lys Glu Phe Lys Ile Lys Val Gly Lys
        275                 280                 285
Lys Glu Thr Glu Thr Lys Tyr Gly Ile Arg Ile Asp Asn Leu Ser Arg
    290                 295                 300
Thr Leu Ile Leu Lys Cys Asn Ser Tyr Arg His Ala Arg Trp Trp Gly
305                 310                 315                 320
Gly Ala Ile Glu Glu Phe Ile Gln Lys His Gly Thr Asn Phe Leu Lys
                325                 330                 335
Asp His Arg Phe Gly Ser Tyr Ala Ala Ile Gln Glu Asn Ala Leu Ala
            340                 345                 350
Lys Trp Tyr Val Asn Ala Lys Gly Tyr Phe Glu Asp Val Ala Asn Ala
        355                 360                 365
Met Glu Glu Ala Asn Glu Glu Ile Phe Ile Thr Asp Trp Trp Leu Ser
    370                 375                 380
Pro Glu Ile Phe Leu Lys Arg Pro Val Val Glu Gly Asn Arg Trp Arg
385                 390                 395                 400
Leu Asp Cys Ile Leu Lys Arg Lys Ala Gln Gln Gly Val Arg Ile Phe
                405                 410                 415
Ile Met Leu Tyr Lys Glu Val Glu Leu Ala Leu Gly Ile Asn Ser Glu
            420                 425                 430
Tyr Thr Lys Arg Thr Leu Met Arg Leu His Pro Asn Ile Lys Val Met
        435                 440                 445
Arg His Pro Asp His Val Ser Ser Thr Val Tyr Leu Trp Ala His His
    450                 455                 460
Glu Lys Leu Val Ile Ile Asp Gln Ser Val Ala Phe Val Gly Gly Ile
465                 470                 475                 480
Asp Leu Ala Tyr Gly Arg Trp Asp Asp Asn Glu His Arg Leu Thr Asp
                485                 490                 495
Val Gly Ser Val Lys Arg Val Thr Ser Gly Pro Ser Leu Gly Ser Leu
            500                 505                 510
Pro Pro Ala Ala Met Glu Ser Met Glu Ser Leu Arg Leu Lys Asp Lys
        515                 520                 525
Asn Glu Pro Val Gln Asn Leu Pro Ile Gln Lys Ser Ile Asp Asp Val
    530                 535                 540
Asp Ser Lys Leu Lys Gly Ile Gly Lys Pro Arg Lys Phe Ser Lys Phe
545                 550                 555                 560
Ser Leu Tyr Lys Gln Leu His Arg His Leu His Asp Ala Asp Ser
                565                 570                 575
Ile Ser Ser Ile Asp Ser Thr Ser Ser Tyr Phe Asn His Tyr Arg Ser
            580                 585                 590
```

-continued

```
His His Asn Leu Ile His Gly Leu Lys Pro His Phe Lys Leu Phe His
        595                 600             605

Pro Ser Ser Glu Ser Glu Gln Gly Leu Thr Arg Pro His Ala Asp Thr
    610             615                 620

Gly Ser Ile Arg Ser Leu Gln Thr Gly Val Gly Glu Leu His Gly Glu
625             630                 635                 640

Thr Arg Phe Trp His Gly Lys Asp Tyr Cys Asn Phe Val Phe Lys Asp
            645                 650                 655

Trp Val Gln Leu Asp Lys Pro Phe Ala Asp Phe Ile Asp Arg Tyr Ser
            660                 665             670

Thr Pro Arg Met Pro Trp His Asp Ile Ala Ser Ala Val His Gly Lys
        675                 680                 685

Ala Ala Arg Asp Val Ala Arg His Phe Ile Gln Arg Trp Asn Phe Thr
690                 695                 700

Lys Ile Met Lys Ser Lys Tyr Arg Ser Leu Ser Tyr Pro Phe Leu Leu
705                 710                 715                 720

Pro Lys Ser Gln Thr Thr Ala His Glu Leu Arg Tyr Gln Val Pro Gly
                725                 730                 735

Ser Val His Ala Asn Val Gln Leu Leu Arg Ser Ala Ala Asp Trp Ser
            740                 745                 750

Ala Gly Ile Lys Tyr His Glu Glu Ser Ile His Ala Ala Tyr Val His
            755                 760                 765

Val Ile Glu Asn Ser Arg His Tyr Ile Tyr Ile Glu Asn Gln Phe Phe
770                 775                 780

Ile Ser Cys Ala Asp Asp Lys Val Val Phe Asn Lys Ile Gly Asp Ala
785                 790                 795                 800

Ile Ala Gln Arg Ile Leu Lys Ala His Arg Glu Asn Gln Lys Tyr Arg
                805                 810                 815

Val Tyr Val Val Ile Pro Leu Leu Pro Gly Phe Glu Gly Asp Ile Ser
                820                 825                 830

Thr Gly Gly Gly Asn Ala Leu Gln Ala Ile Met His Phe Asn Tyr Arg
        835                 840                 845

Thr Met Cys Arg Gly Glu Asn Ser Ile Leu Gly Gln Leu Lys Ala Glu
    850                 855                 860

Leu Gly Asn Gln Trp Ile Asn Tyr Ile Ser Phe Cys Gly Leu Arg Thr
865                 870                 875                 880

His Ala Glu Leu Glu Gly Asn Leu Val Thr Glu Leu Ile Tyr Val His
                885                 890                 895

Ser Lys Leu Leu Ile Ala Asp Asp Asn Thr Val Ile Ile Gly Ser Ala
            900                 905                 910

Asn Ile Asn Asp Arg Ser Met Leu Gly Lys Arg Asp Ser Glu Met Ala
            915                 920                 925

Val Ile Val Gln Asp Thr Glu Thr Val Pro Ser Val Met Asp Gly Lys
        930                 935                 940

Glu Tyr Gln Ala Gly Arg Phe Ala Arg Gly Leu Arg Leu Gln Cys Phe
945                 950                 955                 960

Arg Val Val Leu Gly Tyr Leu Asp Asp Pro Ser Glu Asp Ile Gln Asp
                965                 970                 975

Pro Val Ser Asp Lys Phe Phe Lys Glu Val Trp Val Ser Thr Ala Ala
            980                 985                 990

Arg Asn Ala Thr Ile Tyr Asp Lys Val Phe Arg Cys Leu Pro Asn Asp
            995                 1000                1005
```

```
Glu Val His Asn Leu Ile Gln Leu Arg Asp Phe Ile Asn Lys Pro Val
    1010                1015                1020

Leu Ala Lys Glu Asp Pro Ile Arg Ala Glu Glu Leu Lys Lys Ile
    1025                1030                1035                1040

Arg Gly Phe Leu Val Gln Phe Pro Phe Tyr Phe Leu Ser Glu Glu Ser
                1045                1050                1055

Leu Leu Pro Ser Val Gly Thr Lys Glu Ala Ile Val Pro Met Glu Val
                1060                1065                1070

Trp Thr
```

<210> SEQ ID NO 4
<211> LENGTH: 19
<212> TYPE: PRT
<213> ORGANISM: castor bean

<400> SEQUENCE: 4

```
Gln Arg Ser Met Asp Gly Ala Arg Asp Ser Glu Ile Ala Met Gly Ala
  1               5                  10                  15

Tyr Gln Pro
```

<210> SEQ ID NO 5
<211> LENGTH: 19
<212> TYPE: PRT
<213> ORGANISM: yeast

<400> SEQUENCE: 5

```
Glu Arg Ser Gln Leu Gly Asn Arg Asp Ser Glu Val Ala Ile Leu Ile
  1               5                  10                  15

Arg Asp Thr
```

<210> SEQ ID NO 6
<211> LENGTH: 19
<212> TYPE: PRT
<213> ORGANISM: R83570/261972

<400> SEQUENCE: 6

```
Asp Arg Ser Leu Leu Gly Lys Arg Asp Ser Glu Leu Ala Val Leu Ile
  1               5                  10                  15
Glu Asp Thr
```

<210> SEQ ID NO 7
<211> LENGTH: 24
<212> TYPE: DNA
<213> ORGANISM: oligonucleotide/primer

<400> SEQUENCE: 7
gtattcaatc ctgcatcgcc ttaa                                    24

<210> SEQ ID NO 8
<211> LENGTH: 27
<212> TYPE: DNA
<213> ORGANISM: oligonucleotide/primer

<400> SEQUENCE: 8
gtcatctgcg atgagcacct tgctgtg                                 27

<210> SEQ ID NO 9
<211> LENGTH: 21
<212> TYPE: DNA
<213> ORGANISM: oligonucleotide/primer

<400> SEQUENCE: 9

```
ctagcttata atacgactca c                                              21

<210> SEQ ID NO 10
<211> LENGTH: 21
<212> TYPE: DNA
<213> ORGANISM: oligonucleotide/primer

<400> SEQUENCE: 10
gactctagcc taggcttttg c                                              21

<210> SEQ ID NO 11
<211> LENGTH: 21
<212> TYPE: DNA
<213> ORGANISM: oligonucleotide/primer

<400> SEQUENCE: 11
ctcaggactc aaccaccagt c                                              21

<210> SEQ ID NO 12
<211> LENGTH: 29
<212> TYPE: DNA
<213> ORGANISM: oligonucleotide/primer

<400> SEQUENCE: 12
ggctctagat attaatagta atcaattac                                      29

<210> SEQ ID NO 13
<211> LENGTH: 26
<212> TYPE: DNA
<213> ORGANISM: oligonucleotide/primer

<400> SEQUENCE: 13
cctcacgcat gcaccatggt aatagc                                         26

<210> SEQ ID NO 14
<211> LENGTH: 24
<212> TYPE: DNA
<213> ORGANISM: oligonucleotide/primer

<400> SEQUENCE: 14
ggtgcatgcg tgaggctccg gtgc                                           24

<210> SEQ ID NO 15
<211> LENGTH: 28
<212> TYPE: DNA
<213> ORGANISM: oligonucleotide/primer

<400> SEQUENCE: 15
gtagttttca cggtacctga aatggaag                                       28

<210> SEQ ID NO 16
<211> LENGTH: 3425
<212> TYPE: DNA
<213> ORGANISM: Homo sapiens
<220> FEATURE:
<221> NAME/KEY: CDS
<222> LOCATION: (64)..(2862)

<400> SEQUENCE: 16
tgcagctccg gtctgctctc ttggctcggg aaccccgcg  ggcgctggct ccgtctgcca    60 ggg atg acg gcg acc cct gag agc ctc ttc ccc act ggg gac gaa ctg    108
    Met Thr Ala Thr Pro Glu Ser Leu Phe Pro Thr Gly Asp Glu Leu
    1               5                   10                  15
```

```
gac tcc agc cag ctc cag atg gag tcc gat gag gtg gac acc ctg aag       156
Asp Ser Ser Gln Leu Gln Met Glu Ser Asp Glu Val Asp Thr Leu Lys
                 20                  25                  30 gag gga gag gac cca gcc gac cgg atg cac ccg ttt ctg gcc atc tat       204
Glu Gly Glu Asp Pro Ala Asp Arg Met His Pro Phe Leu Ala Ile Tyr
             35                  40                  45 gag ctt cag tct ctg aaa gtg cac ccc ttg gtg ttc gca cct ggg gtc       252
Glu Leu Gln Ser Leu Lys Val His Pro Leu Val Phe Ala Pro Gly Val
         50                  55                  60 cct gtc aca gcc cag gtg gtg ggc acc gaa aga tat acc agc gga tcc       300
Pro Val Thr Ala Gln Val Val Gly Thr Glu Arg Tyr Thr Ser Gly Ser
     65                  70                  75 aag gtg gga acc tgc act ctg tat tct gtc cgc ttg act cac ggc gac       348
Lys Val Gly Thr Cys Thr Leu Tyr Ser Val Arg Leu Thr His Gly Asp
 80                  85                  90                  95 ttt tcc tgg aca acc aag aag aaa tac cgt cat ttt cag gag ctg cat       396
Phe Ser Trp Thr Thr Lys Lys Lys Tyr Arg His Phe Gln Glu Leu His
                100                 105                 110 cgg gac ctc ctg aga cac aaa gtc ttg atg agt ctg ctc cct ctg gct       444
Arg Asp Leu Leu Arg His Lys Val Leu Met Ser Leu Leu Pro Leu Ala
            115                 120                 125 cga ttt gcc gtt gcc tat tct cca gcc cga gat gca ggc aac aga gag       492
Arg Phe Ala Val Ala Tyr Ser Pro Ala Arg Asp Ala Gly Asn Arg Glu
        130                 135                 140 atg ccc tct cta ccc cgg gca ggt cct gag ggc tcc acc aga cat gca       540
Met Pro Ser Leu Pro Arg Ala Gly Pro Glu Gly Ser Thr Arg His Ala
    145                 150                 155 gcc agc aaa cag aaa tac ctg gag aat tac ctc aac cgt ctc ttg acc       588
Ala Ser Lys Gln Lys Tyr Leu Glu Asn Tyr Leu Asn Arg Leu Leu Thr
160                 165                 170                 175 atg tct ttc tat cgc aac tac cat gcc atg aca gag ttc ctg gaa gtc       636
Met Ser Phe Tyr Arg Asn Tyr His Ala Met Thr Glu Phe Leu Glu Val
                180                 185                 190 agt cag ctg tcc ttt atc ccg gac ttg ggc cgc aaa gga ctg gag ggg       684
Ser Gln Leu Ser Phe Ile Pro Asp Leu Gly Arg Lys Gly Leu Glu Gly
            195                 200                 205 atg atc cgg aag cgc tca ggt ggc cac cgt gtt cct ggc ctc acc tgc       732
Met Ile Arg Lys Arg Ser Gly Gly His Arg Val Pro Gly Leu Thr Cys
        210                 215                 220 tgt ggc cga gac caa gtt tgt tat cgc tgg tcc aag agg tgg ctg gtg       780
Cys Gly Arg Asp Gln Val Cys Tyr Arg Trp Ser Lys Arg Trp Leu Val
    225                 230                 235 gtg aag gac tcc ttc ctg ctg tac atg tgc ctc gag aca ggt gcc atc       828
Val Lys Asp Ser Phe Leu Leu Tyr Met Cys Leu Glu Thr Gly Ala Ile
240                 245                 250                 255 tca ttt gtt cag ctc ttt gac cct ggc ttt gag gtg caa gtg ggg aaa       876
Ser Phe Val Gln Leu Phe Asp Pro Gly Phe Glu Val Gln Val Gly Lys
                260                 265                 270 agg agc acg gag gca cgg cac ggc gtg cgg atc gat acc tcc cac agg       924
Arg Ser Thr Glu Ala Arg His Gly Val Arg Ile Asp Thr Ser His Arg
            275                 280                 285 tcc ttg att ctc aag tgc agc agc tac cgg cag gca cgg tgg tgg gcc       972
Ser Leu Ile Leu Lys Cys Ser Ser Tyr Arg Gln Ala Arg Trp Trp Ala
        290                 295                 300 caa gag atc act gag ctg gca cag ggc cca ggc aga gac ttc cta cag      1020
Gln Glu Ile Thr Glu Leu Ala Gln Gly Pro Gly Arg Asp Phe Leu Gln
    305                 310                 315 ctg cac cgg cat gac agc tac gcc cca ccc cgg cct ggg acc ttg gcc      1068
Leu His Arg His Asp Ser Tyr Ala Pro Pro Arg Pro Gly Thr Leu Ala
```

```
                                                    -continued
320                 325                 330                 335
cgg tgg ttt gtg aat ggg gca ggt tac ttt gct gct gtg gca gat gcc      1116
Arg Trp Phe Val Asn Gly Ala Gly Tyr Phe Ala Ala Val Ala Asp Ala
                340                 345                 350 atc ctt cga gct caa gag gag att ttc atc aca gac tgg tgg ttg agt      1164
Ile Leu Arg Ala Gln Glu Glu Ile Phe Ile Thr Asp Trp Trp Leu Ser
            355                 360                 365 cct gag gtt tac ctg aag cgt ccg gcc cat tca gat gac tgg aga ctg      1212
Pro Glu Val Tyr Leu Lys Arg Pro Ala His Ser Asp Asp Trp Arg Leu
        370                 375                 380 gac att atg ctc aag agg aag gcg gag gag ggt gtc cgt gtg tct att      1260
Asp Ile Met Leu Lys Arg Lys Ala Glu Glu Gly Val Arg Val Ser Ile
    385                 390                 395 ctg ctg ttt aaa gaa gtg gaa ttg gcc ttg ggc atc aac agt ggc tat      1308
Leu Leu Phe Lys Glu Val Glu Leu Ala Leu Gly Ile Asn Ser Gly Tyr
400                 405                 410                 415 agc aag agg gcg ctg atg ctg ctg cac ccc aac ata aag gtg atg cgt      1356
Ser Lys Arg Ala Leu Met Leu Leu His Pro Asn Ile Lys Val Met Arg
                420                 425                 430 cac cca gac caa gtg acg ttg tgg gcc cat cat gag aag ctc ctg gtg      1404
His Pro Asp Gln Val Thr Leu Trp Ala His His Glu Lys Leu Leu Val
            435                 440                 445 gtg gac caa gtg gta gca ttc ctg ggg gga ctg gac ctt gcc tat ggc      1452
Val Asp Gln Val Val Ala Phe Leu Gly Gly Leu Asp Leu Ala Tyr Gly
        450                 455                 460 cgc tgg gat gac ctg cac tac cga ctg act gac ctt gga gac tcc tct      1500
Arg Trp Asp Asp Leu His Tyr Arg Leu Thr Asp Leu Gly Asp Ser Ser
    465                 470                 475 gaa tca gct gcc tcc cag cct ccc acc ccg cgc cca gac tca cca gcc      1548
Glu Ser Ala Ala Ser Gln Pro Pro Thr Pro Arg Pro Asp Ser Pro Ala
480                 485                 490                 495 acc cca gac ctc tct cac aac caa ttc ttc tgg ctg ggc aag gac tac      1596
Thr Pro Asp Leu Ser His Asn Gln Phe Phe Trp Leu Gly Lys Asp Tyr
                500                 505                 510 agc aat ctt atc acc aag gac tgg gtg cag ctg gac cgg cct ttc gaa      1644
Ser Asn Leu Ile Thr Lys Asp Trp Val Gln Leu Asp Arg Pro Phe Glu
            515                 520                 525 gat ttc att gac agg gag acg acc cct cgg atg cca tgg cgg gac gtt      1692
Asp Phe Ile Asp Arg Glu Thr Thr Pro Arg Met Pro Trp Arg Asp Val
        530                 535                 540 ggg gtg gtc gtc cat ggc cta ccg gcc cgg gac ctt gcc cgg cac ttc      1740
Gly Val Val Val His Gly Leu Pro Ala Arg Asp Leu Ala Arg His Phe
    545                 550                 555 atc cag cgc tgg aac ttc acc aag acc acc aag gcc aag tac aag act      1788
Ile Gln Arg Trp Asn Phe Thr Lys Thr Thr Lys Ala Lys Tyr Lys Thr
560                 565                 570                 575 ccc aca tac ccc tac ctg ctt ccc aag tct acc agc acg gcc aat cag      1836
Pro Thr Tyr Pro Tyr Leu Leu Pro Lys Ser Thr Ser Thr Ala Asn Gln
                580                 585                 590 ctc ccc ttc aca ctt cca gga ggg cag tgc acc acc gta cag gtc ttg      1884
Leu Pro Phe Thr Leu Pro Gly Gly Gln Cys Thr Thr Val Gln Val Leu
            595                 600                 605 cga tca gtg gac cgc tgg tca gca ggg act ctg gag aac tcc atc ctc      1932
Arg Ser Val Asp Arg Trp Ser Ala Gly Thr Leu Glu Asn Ser Ile Leu
        610                 615                 620 aat gcc tac ctg cac acc atc agg ggg agc cag cac ttc ctc tac att      1980
Asn Ala Tyr Leu His Thr Ile Arg Gly Ser Gln His Phe Leu Tyr Ile
    625                 630                 635 gag aat cag ttc ttc att agc tgc tca gat ggg cgg acg gtt ctg aac      2028
Glu Asn Gln Phe Phe Ile Ser Cys Ser Asp Gly Arg Thr Val Leu Asn
```

```
                                                      -continued
Glu Asn Gln Phe Phe Ile Ser Cys Ser Asp Gly Arg Thr Val Leu Asn
640                 645                 650                 655 aag gtg ggc gat gag att gtg gac aga atc ctg aag gcc cac aaa cag      2076
Lys Val Gly Asp Glu Ile Val Asp Arg Ile Leu Lys Ala His Lys Gln
                    660                 665                 670 ggg tgg tgt tac cga gtc tac gtg ctt ttg ccc tta ctc cct ggc ttc      2124
Gly Trp Cys Tyr Arg Val Tyr Val Leu Leu Pro Leu Leu Pro Gly Phe
                675                 680                 685 gag ggt gac atc tcc acg ggc ggt ggc aac tcc atc cag gcc att ctg      2172
Glu Gly Asp Ile Ser Thr Gly Gly Gly Asn Ser Ile Gln Ala Ile Leu
            690                 695                 700 cac ttt act tac agg acc ctg tgt cgt ggg gag tat tca atc ctg cat      2220
His Phe Thr Tyr Arg Thr Leu Cys Arg Gly Glu Tyr Ser Ile Leu His
        705                 710                 715 cgc ctt aaa gca gcc atg ggg aca gca tgg cgg gac tat att tcc atc      2268
Arg Leu Lys Ala Ala Met Gly Thr Ala Trp Arg Asp Tyr Ile Ser Ile
720                 725                 730                 735 tgc ggg ctt cgt aca cac gga gag ctg ggc ggg cac ccc gtc tcg gag      2316
Cys Gly Leu Arg Thr His Gly Glu Leu Gly Gly His Pro Val Ser Glu
                    740                 745                 750 ctc atc tac atc cac agc aag gtg ctc atc gca gat gac cgg aca gtc      2364
Leu Ile Tyr Ile His Ser Lys Val Leu Ile Ala Asp Asp Arg Thr Val
                755                 760                 765 atc att ggt tct gca aac atc aat gac cgg agc ttg ctg ggg aag cgg      2412
Ile Ile Gly Ser Ala Asn Ile Asn Asp Arg Ser Leu Leu Gly Lys Arg
            770                 775                 780 gac agt gag ctg gcc gtg cta atc gag gac aca gag acg gaa cca tcc      2460
Asp Ser Glu Leu Ala Val Leu Ile Glu Asp Thr Glu Thr Glu Pro Ser
        785                 790                 795 ctc atg aat ggg gca gag tat cag gcg ggc agg ttt gcc ttg agt ctg      2508
Leu Met Asn Gly Ala Glu Tyr Gln Ala Gly Arg Phe Ala Leu Ser Leu
800                 805                 810                 815 cgg aag cac tgc ttc ggt gtg att ctt gga gca aat acc cgg cca gac      2556
Arg Lys His Cys Phe Gly Val Ile Leu Gly Ala Asn Thr Arg Pro Asp
                    820                 825                 830 ttg gat ctc cga gac ccc atc tgt gat gac ttc ttc cag ttg tgg caa      2604
Leu Asp Leu Arg Asp Pro Ile Cys Asp Asp Phe Phe Gln Leu Trp Gln
                835                 840                 845 gac atg gct gag agc aac gcc aat atc tat gag cag atc ttc cgc tgc      2652
Asp Met Ala Glu Ser Asn Ala Asn Ile Tyr Glu Gln Ile Phe Arg Cys
            850                 855                 860 ctg cca tcc aat gcc acg cgt tcc ctg cgg act ctc cgg gag tac gtg      2700
Leu Pro Ser Asn Ala Thr Arg Ser Leu Arg Thr Leu Arg Glu Tyr Val
        865                 870                 875 gcc gtg gag ccc ttg gcc acg gtc agt ccc ccc ttg gct cgg tct gag      2748
Ala Val Glu Pro Leu Ala Thr Val Ser Pro Pro Leu Ala Arg Ser Glu
880                 885                 890                 895 ctc acc cag gtc cag ggc cac ctg gtc cac ttc ccc ctc aag ttc cta      2796
Leu Thr Gln Val Gln Gly His Leu Val His Phe Pro Leu Lys Phe Leu
                    900                 905                 910 gag gat gag tct ttg ctg ccc ccg ctg ggt agc aag gag ggc atg atc      2844
Glu Asp Glu Ser Leu Leu Pro Pro Leu Gly Ser Lys Glu Gly Met Ile
                915                 920                 925 ccc cta gaa gtg tgg aca tagttgaggc ccccgtcagg gagaggtcac              2892
Pro Leu Glu Val Trp Thr
            930 cagctgctgt gccccaccac gtctggctcc ctgccccta accccaagga ctgagggcag      2952 tgcccttga gatctgggga ggcaggcatt cctgaaggga actagaggtg ttacagagga      3012
```

-continued

```
ccccttacgtg agaaatagct gaaaagggca ctcccaaccc tgggctgggg aggaggagag   3072
agtcccagag ctcatccccc ctgctgccca gtgcaaacca cttctccatg ctgcaaagga   3132
gaagcacagc tcctgccagg gtgagcaggg tcaagcctct tattccagga gaagggggct   3192 ctgcccagg ccctactacc cattgttccc ttcctcttcc tgcccttgaa cccctccct    3252 gtccagggc cctcccagcc cattgctgcc aaggtggagg gaaggataaa gccacttctg   3312
gcttcagccc ccaccagggg aaggaaggag ggcacattaa ctccctccac cagcctgctg   3372
acagacacta actttgtatc cgttcaataa gcatttcata aaaaaaaaaa aaa          3425
```

<210> SEQ ID NO 17
<211> LENGTH: 933
<212> TYPE: PRT
<213> ORGANISM: Homo sapiens

<400> SEQUENCE: 17

```
Met Thr Ala Thr Pro Glu Ser Leu Phe Pro Thr Gly Asp Glu Leu Asp
  1               5                  10                  15

Ser Ser Gln Leu Gln Met Glu Ser Asp Glu Val Asp Thr Leu Lys Glu
                 20                  25                  30

Gly Glu Asp Pro Ala Asp Arg Met His Pro Phe Leu Ala Ile Tyr Glu
             35                  40                  45

Leu Gln Ser Leu Lys Val His Pro Leu Val Phe Ala Pro Gly Val Pro
         50                  55                  60

Val Thr Ala Gln Val Val Gly Thr Glu Arg Tyr Thr Ser Gly Ser Lys
 65                  70                  75                  80

Val Gly Thr Cys Thr Leu Tyr Ser Val Arg Leu Thr His Gly Asp Phe
                 85                  90                  95

Ser Trp Thr Thr Lys Lys Lys Tyr Arg His Phe Gln Glu Leu His Arg
            100                 105                 110

Asp Leu Leu Arg His Lys Val Leu Met Ser Leu Leu Pro Leu Ala Arg
        115                 120                 125

Phe Ala Val Ala Tyr Ser Pro Ala Arg Asp Ala Gly Asn Arg Glu Met
    130                 135                 140

Pro Ser Leu Pro Arg Ala Gly Pro Glu Gly Ser Thr Arg His Ala Ala
145                 150                 155                 160

Ser Lys Gln Lys Tyr Leu Glu Asn Tyr Leu Asn Arg Leu Leu Thr Met
                165                 170                 175

Ser Phe Tyr Arg Asn Tyr His Ala Met Thr Glu Phe Leu Glu Val Ser
            180                 185                 190

Gln Leu Ser Phe Ile Pro Asp Leu Gly Arg Lys Gly Leu Glu Gly Met
        195                 200                 205

Ile Arg Lys Arg Ser Gly Gly His Arg Val Pro Gly Leu Thr Cys Cys
    210                 215                 220

Gly Arg Asp Gln Val Cys Tyr Arg Trp Ser Lys Arg Trp Leu Val Val
225                 230                 235                 240

Lys Asp Ser Phe Leu Leu Tyr Met Cys Leu Glu Thr Gly Ala Ile Ser
                245                 250                 255

Phe Val Gln Leu Phe Asp Pro Gly Phe Glu Val Gln Val Gly Lys Arg
            260                 265                 270

Ser Thr Glu Ala Arg His Gly Val Arg Ile Asp Thr Ser His Arg Ser
        275                 280                 285

Leu Ile Leu Lys Cys Ser Ser Tyr Arg Gln Ala Arg Trp Trp Ala Gln
    290                 295                 300
```

-continued

```
Glu Ile Thr Glu Leu Ala Gln Gly Pro Gly Arg Asp Phe Leu Gln Leu
305                 310                 315                 320

His Arg His Asp Ser Tyr Ala Pro Pro Arg Pro Gly Thr Leu Ala Arg
                325                 330                 335

Trp Phe Val Asn Gly Ala Gly Tyr Phe Ala Ala Val Ala Asp Ala Ile
                340                 345                 350

Leu Arg Ala Gln Glu Glu Ile Phe Ile Thr Asp Trp Trp Leu Ser Pro
            355                 360                 365

Glu Val Tyr Leu Lys Arg Pro Ala His Ser Asp Asp Trp Arg Leu Asp
        370                 375                 380

Ile Met Leu Lys Arg Lys Ala Glu Glu Gly Val Arg Val Ser Ile Leu
385                 390                 395                 400

Leu Phe Lys Glu Val Glu Leu Ala Leu Gly Ile Asn Ser Gly Tyr Ser
                405                 410                 415

Lys Arg Ala Leu Met Leu Leu His Pro Asn Ile Lys Val Met Arg His
                420                 425                 430

Pro Asp Gln Val Thr Leu Trp Ala His His Glu Lys Leu Leu Val Val
            435                 440                 445

Asp Gln Val Val Ala Phe Leu Gly Gly Leu Asp Leu Ala Tyr Gly Arg
        450                 455                 460

Trp Asp Asp Leu His Tyr Arg Leu Thr Asp Leu Gly Asp Ser Ser Glu
465                 470                 475                 480

Ser Ala Ala Ser Gln Pro Pro Thr Pro Arg Pro Asp Ser Pro Ala Thr
                485                 490                 495

Pro Asp Leu Ser His Asn Gln Phe Phe Trp Leu Gly Lys Asp Tyr Ser
            500                 505                 510

Asn Leu Ile Thr Lys Asp Trp Val Gln Leu Asp Arg Pro Phe Glu Asp
        515                 520                 525

Phe Ile Asp Arg Glu Thr Thr Pro Arg Met Pro Trp Arg Asp Val Gly
    530                 535                 540

Val Val His Gly Leu Pro Ala Arg Asp Leu Ala Arg His Phe Ile
545                 550                 555                 560

Gln Arg Trp Asn Phe Thr Lys Thr Thr Lys Ala Lys Tyr Lys Thr Pro
                565                 570                 575

Thr Tyr Pro Tyr Leu Leu Pro Lys Ser Thr Ser Thr Ala Asn Gln Leu
            580                 585                 590

Pro Phe Thr Leu Pro Gly Gly Gln Cys Thr Thr Val Gln Val Leu Arg
        595                 600                 605

Ser Val Asp Arg Trp Ser Ala Gly Thr Leu Glu Asn Ser Ile Leu Asn
610                 615                 620

Ala Tyr Leu His Thr Ile Arg Gly Ser Gln His Phe Leu Tyr Ile Glu
625                 630                 635                 640

Asn Gln Phe Phe Ile Ser Cys Ser Asp Gly Arg Thr Val Leu Asn Lys
                645                 650                 655

Val Gly Asp Glu Ile Val Asp Arg Ile Leu Lys Ala His Lys Gln Gly
            660                 665                 670

Trp Cys Tyr Arg Val Tyr Val Leu Leu Pro Leu Leu Pro Gly Phe Glu
        675                 680                 685

Gly Asp Ile Ser Thr Gly Gly Asn Ser Ile Gln Ala Ile Leu His
    690                 695                 700

Phe Thr Tyr Arg Thr Leu Cys Arg Gly Glu Tyr Ser Ile Leu His Arg
705                 710                 715                 720

Leu Lys Ala Ala Met Gly Thr Ala Trp Arg Asp Tyr Ile Ser Ile Cys
```

```
                    725                 730                 735
Gly Leu Arg Thr His Gly Glu Leu Gly Gly His Pro Val Ser Glu Leu
                740                 745                 750

Ile Tyr Ile His Ser Lys Val Leu Ile Ala Asp Asp Arg Thr Val Ile
            755                 760                 765

Ile Gly Ser Ala Asn Ile Asn Asp Arg Ser Leu Leu Gly Lys Arg Asp
        770                 775                 780

Ser Glu Leu Ala Val Leu Ile Glu Asp Thr Glu Thr Glu Pro Ser Leu
785                 790                 795                 800

Met Asn Gly Ala Glu Tyr Gln Ala Gly Arg Phe Ala Leu Ser Leu Arg
                805                 810                 815

Lys His Cys Phe Gly Val Ile Leu Gly Ala Asn Thr Arg Pro Asp Leu
            820                 825                 830

Asp Leu Arg Asp Pro Ile Cys Asp Asp Phe Phe Gln Leu Trp Gln Asp
        835                 840                 845

Met Ala Glu Ser Asn Ala Asn Ile Tyr Glu Gln Ile Phe Arg Cys Leu
850                 855                 860

Pro Ser Asn Ala Thr Arg Ser Leu Arg Thr Leu Arg Glu Tyr Val Ala
865                 870                 875                 880

Val Glu Pro Leu Ala Thr Val Ser Pro Pro Leu Ala Arg Ser Glu Leu
                885                 890                 895

Thr Gln Val Gln Gly His Leu Val His Phe Pro Leu Lys Phe Leu Glu
            900                 905                 910

Asp Glu Ser Leu Leu Pro Pro Leu Gly Ser Lys Glu Gly Met Ile Pro
        915                 920                 925

Leu Glu Val Trp Thr
    930

<210> SEQ ID NO 18
<211> LENGTH: 3114
<212> TYPE: DNA
<213> ORGANISM: Homo sapiens
<220> FEATURE:
<221> NAME/KEY: CDS
<222> LOCATION: (52)..(2964)

<400> SEQUENCE: 18
gcggcccctt cgccctgcag cccctttgct tttactctgt ccaaagttaa c atg tca        57
                                                        Met Ser
                                                          1 ctg aaa aac gag cca cgg gta aat acc tct gca ctg cag aaa att gct      105
Leu Lys Asn Glu Pro Arg Val Asn Thr Ser Ala Leu Gln Lys Ile Ala
        5                   10                  15 gct gac atg agt aat atc ata gaa aat ctg gac acg cgg gaa ctc cac      153
Ala Asp Met Ser Asn Ile Ile Glu Asn Leu Asp Thr Arg Glu Leu His
    20                  25                  30 ttt gag gga gag gag gta gac tac gac gtg tct ccc agc gat ccc aag      201
Phe Glu Gly Glu Glu Val Asp Tyr Asp Val Ser Pro Ser Asp Pro Lys
35                  40                  45                  50 ata caa gaa gtg tat atc cct ttc tct gct att tat aac act caa gga      249
Ile Gln Glu Val Tyr Ile Pro Phe Ser Ala Ile Tyr Asn Thr Gln Gly
                55                  60                  65 ttt aag gag cct aat ata cag acg tat ctc tcc ggc tgt cca ata aaa      297
Phe Lys Glu Pro Asn Ile Gln Thr Tyr Leu Ser Gly Cys Pro Ile Lys
            70                  75                  80 gca caa gtt ctg gaa gtg gaa cgc ttc aca tct aca aca agg gta cca      345
Ala Gln Val Leu Glu Val Glu Arg Phe Thr Ser Thr Thr Arg Val Pro
        85                  90                  95
```

-continued

| | | |
|---|---|---|
| agt att aat ctt tac act att gaa tta aca cat ggg gaa ttt aaa tgg<br>Ser Ile Asn Leu Tyr Thr Ile Glu Leu Thr His Gly Glu Phe Lys Trp<br>100                        105                        110 | 393 |
| caa gtt aag agg aaa ttc aag cat ttt caa gaa ttt cac aga gag ctg<br>Gln Val Lys Arg Lys Phe Lys His Phe Gln Glu Phe His Arg Glu Leu<br>115                        120                        125                        130 | 441 |
| ctc aag tac aaa gcc ttt atc cgc atc ccc att ccc act aga aga cac<br>Leu Lys Tyr Lys Ala Phe Ile Arg Ile Pro Ile Pro Thr Arg Arg His<br>                        135                        140                        145 | 489 |
| acg ttt agg agg caa aac gtc aga gag gag cct cga gag atg ccc agt<br>Thr Phe Arg Arg Gln Asn Val Arg Glu Glu Pro Arg Glu Met Pro Ser<br>                  150                        155                        160 | 537 |
| ttg ccc cgt tca tct gaa aac atg ata aga gaa gaa caa ttc ctt ggt<br>Leu Pro Arg Ser Ser Glu Asn Met Ile Arg Glu Glu Gln Phe Leu Gly<br>                165                        170                        175 | 585 |
| aga aga aaa caa ctg gaa gat tac ttg aca aag ata cta aaa atg ccc<br>Arg Arg Lys Gln Leu Glu Asp Tyr Leu Thr Lys Ile Leu Lys Met Pro<br>180                        185                        190 | 633 |
| atg tat aga aac tat cat gcc aca aca gag ttt ctt gat ata agc cag<br>Met Tyr Arg Asn Tyr His Ala Thr Thr Glu Phe Leu Asp Ile Ser Gln<br>195                        200                        205                        210 | 681 |
| ctg tct ttc atc cat gat ttg gga cca aag ggc ata gaa ggt atg ata<br>Leu Ser Phe Ile His Asp Leu Gly Pro Lys Gly Ile Glu Gly Met Ile<br>                        215                        220                        225 | 729 |
| atg aaa aga tct gga gga cac aga ata cca ggc ttg aat tgc tgt ggt<br>Met Lys Arg Ser Gly Gly His Arg Ile Pro Gly Leu Asn Cys Cys Gly<br>                230                        235                        240 | 777 |
| cag gga aga gcc tgc tac aga tgg tca aaa aga tgg tta ata gtg aaa<br>Gln Gly Arg Ala Cys Tyr Arg Trp Ser Lys Arg Trp Leu Ile Val Lys<br>                        245                        250                        255 | 825 |
| gat tcc ttt tta ttg tat atg aaa cca gac agc ggt gcc att gcc ttc<br>Asp Ser Phe Leu Leu Tyr Met Lys Pro Asp Ser Gly Ala Ile Ala Phe<br>260                        265                        270 | 873 |
| gtc ctg ctg gta gac aaa gaa ttc aaa att aag gtg ggg aag aag gag<br>Val Leu Leu Val Asp Lys Glu Phe Lys Ile Lys Val Gly Lys Lys Glu<br>275                        280                        285                        290 | 921 |
| aca gaa acg aaa tat gga atc cga att gat aat ctt tca agg aca ctt<br>Thr Glu Thr Lys Tyr Gly Ile Arg Ile Asp Asn Leu Ser Arg Thr Leu<br>                        295                        300                        305 | 969 |
| att tta aaa tgc aac agc tat aga cat gct cgg tgg tgg gga ggg gct<br>Ile Leu Lys Cys Asn Ser Tyr Arg His Ala Arg Trp Trp Gly Gly Ala<br>                    310                        315                        320 | 1017 |
| ata gaa gaa ttc atc cag aaa cat ggc acc aac ttt ctc aaa gat cat<br>Ile Glu Glu Phe Ile Gln Lys His Gly Thr Asn Phe Leu Lys Asp His<br>                        325                        330                        335 | 1065 |
| cga ttt ggg tca tat gct gct atc caa gag aat gct tta gct aaa tgg<br>Arg Phe Gly Ser Tyr Ala Ala Ile Gln Glu Asn Ala Leu Ala Lys Trp<br>340                        345                        350 | 1113 |
| tat gtt aat gcc aaa gga tat ttt gaa gat gtg gca aat gca atg gaa<br>Tyr Val Asn Ala Lys Gly Tyr Phe Glu Asp Val Ala Asn Ala Met Glu<br>355                        360                        365                        370 | 1161 |
| gag gca aat gaa gag att ttt atc aca gac tgg tgg ctg agt cca gaa<br>Glu Ala Asn Glu Glu Ile Phe Ile Thr Asp Trp Trp Leu Ser Pro Glu<br>                    375                        380                        385 | 1209 |
| atc ttc ctg aaa cgc cca gtg gtt gag gga aat cgt tgg agg ttg gac<br>Ile Phe Leu Lys Arg Pro Val Val Glu Gly Asn Arg Trp Arg Leu Asp<br>                        390                        395                        400 | 1257 |
| tgc att ctt aaa cga aaa gca caa caa gga gtg agg atc ttc ata atg<br>Cys Ile Leu Lys Arg Lys Ala Gln Gln Gly Val Arg Ile Phe Ile Met | 1305 |

```
                405                 410                 415
ctc tac aaa gag gtg gaa ctc gct ctt ggc atc aat agt gaa tac acc     1353
Leu Tyr Lys Glu Val Glu Leu Ala Leu Gly Ile Asn Ser Glu Tyr Thr
        420                 425                 430 aag agg act ttg atg cgt cta cat ccc aac ata aag gtg atg aga cac     1401
Lys Arg Thr Leu Met Arg Leu His Pro Asn Ile Lys Val Met Arg His
435                 440                 445                 450 ccg gat cat gtg tca tcc acc gtc tat ttg tgg gct cac cat gag aag     1449
Pro Asp His Val Ser Ser Thr Val Tyr Leu Trp Ala His His Glu Lys
                455                 460                 465 ctt gtc atc att gac caa tcg gtg gcc ttt gtg gga ggg att gac ctg     1497
Leu Val Ile Ile Asp Gln Ser Val Ala Phe Val Gly Gly Ile Asp Leu
                470                 475                 480 gcc tat gga agg tgg gac gac aat gag cac aga ctc aca gac gtg ggc     1545
Ala Tyr Gly Arg Trp Asp Asp Asn Glu His Arg Leu Thr Asp Val Gly
            485                 490                 495 agt gtg aag cgg gtc act tca gga ccg tct ctg ggt tcc ctc cca cct     1593
Ser Val Lys Arg Val Thr Ser Gly Pro Ser Leu Gly Ser Leu Pro Pro
        500                 505                 510 gcc gca atg gag tct atg gaa tcc tta aga ctc aaa gat aaa aat gag     1641
Ala Ala Met Glu Ser Met Glu Ser Leu Arg Leu Lys Asp Lys Asn Glu
515                 520                 525                 530 cct gtt caa aac cta ccc atc cag aag agt att gat gat gtg gat tca     1689
Pro Val Gln Asn Leu Pro Ile Gln Lys Ser Ile Asp Asp Val Asp Ser
                535                 540                 545 aaa ctg aaa gga ata gga aag cca aga aag ttc tcc aaa ttt agt ctc     1737
Lys Leu Lys Gly Ile Gly Lys Pro Arg Lys Phe Ser Lys Phe Ser Leu
                550                 555                 560 tac aag cag ctc cac agg cac cac ctg cac gac gca gat agc atc agc     1785
Tyr Lys Gln Leu His Arg His His Leu His Asp Ala Asp Ser Ile Ser
            565                 570                 575 agc att gac agc acc tcc agt tat ttt aat cac tat aga agt cat cac     1833
Ser Ile Asp Ser Thr Ser Ser Tyr Phe Asn His Tyr Arg Ser His His
        580                 585                 590 aat tta atc cat ggt tta aaa ccc cac ttc aaa ctc ttt cac ccg tcc     1881
Asn Leu Ile His Gly Leu Lys Pro His Phe Lys Leu Phe His Pro Ser
595                 600                 605                 610 agt gag tct gag caa gga ctc act aga cct cat gct gat acc ggg tcc     1929
Ser Glu Ser Glu Gln Gly Leu Thr Arg Pro His Ala Asp Thr Gly Ser
                615                 620                 625 atc cgt agt tta cag aca ggt gtg gga gag ctg cat ggg gaa acc aga     1977
Ile Arg Ser Leu Gln Thr Gly Val Gly Glu Leu His Gly Glu Thr Arg
                630                 635                 640 ttc tgg cat gga aag gac tac tgc aat ttc gtc ttc aaa gac tgg gtt     2025
Phe Trp His Gly Lys Asp Tyr Cys Asn Phe Val Phe Lys Asp Trp Val
            645                 650                 655 caa ctt gat aaa cct ttt gct gat ttc att gac agg tac tcc acg ccc     2073
Gln Leu Asp Lys Pro Phe Ala Asp Phe Ile Asp Arg Tyr Ser Thr Pro
        660                 665                 670 cgg atg ccc tgg cat gac att gcc tct gca gtc cac ggg aag gcg gct     2121
Arg Met Pro Trp His Asp Ile Ala Ser Ala Val His Gly Lys Ala Ala
675                 680                 685                 690 cgt gat gtg gca cgt cac ttc atc cag cgc tgg aac ttc aca aaa att     2169
Arg Asp Val Ala Arg His Phe Ile Gln Arg Trp Asn Phe Thr Lys Ile
                695                 700                 705 atg aaa tca aaa tat cgg tcc ctt tct tat cct ttt ctg ctt cca aag     2217
Met Lys Ser Lys Tyr Arg Ser Leu Ser Tyr Pro Phe Leu Leu Pro Lys
                710                 715                 720 tct caa aca aca gcc cat gag ttg aga tat caa gtg cct ggg tct gtc     2265
```

```
                                                        -continued

Ser Gln Thr Thr Ala His Glu Leu Arg Tyr Gln Val Pro Gly Ser Val
        725                 730                 735 cat gct aac gta cag ttg ctc cgc tct gct gct gat tgg tct gct ggt       2313
His Ala Asn Val Gln Leu Leu Arg Ser Ala Ala Asp Trp Ser Ala Gly
        740                 745                 750 ata aag tac cat gaa gag tcc atc cac gcc gct tac gtc cat gtg ata       2361
Ile Lys Tyr His Glu Glu Ser Ile His Ala Ala Tyr Val His Val Ile
755                 760                 765                 770 gag aac agc agg cac tat atc tat atc gaa aac cag ttt ttc ata agc       2409
Glu Asn Ser Arg His Tyr Ile Tyr Ile Glu Asn Gln Phe Phe Ile Ser
                775                 780                 785 tgt gct gat gac aaa gtt gtg ttc aac aag ata ggc gat gcc att gcc       2457
Cys Ala Asp Asp Lys Val Val Phe Asn Lys Ile Gly Asp Ala Ile Ala
            790                 795                 800 cag agg atc ctg aaa gct cac agg gaa aac cag aaa tac cgg gta tat       2505
Gln Arg Ile Leu Lys Ala His Arg Glu Asn Gln Lys Tyr Arg Val Tyr
        805                 810                 815 gtc gtg ata cca ctt ctg cca ggg ttc gaa gga gac att tca acc ggc       2553
Val Val Ile Pro Leu Leu Pro Gly Phe Glu Gly Asp Ile Ser Thr Gly
        820                 825                 830 gga gga aat gct cta cag gca atc atg cac ttc aac tac aga acc atg       2601
Gly Gly Asn Ala Leu Gln Ala Ile Met His Phe Asn Tyr Arg Thr Met
835                 840                 845                 850 tgc aga gga gaa aat tcc atc ctt gga cag tta aaa gca gag ctt ggt       2649
Cys Arg Gly Glu Asn Ser Ile Leu Gly Gln Leu Lys Ala Glu Leu Gly
                855                 860                 865 aat cag tgg ata aat tac ata tca ttc tgt ggt ctt aga aca cat gca       2697
Asn Gln Trp Ile Asn Tyr Ile Ser Phe Cys Gly Leu Arg Thr His Ala
            870                 875                 880 gag ctc gaa gga aac cta gtc act gag ctt atc tat gtc cac agc aag       2745
Glu Leu Glu Gly Asn Leu Val Thr Glu Leu Ile Tyr Val His Ser Lys
        885                 890                 895 ttg tta att gct gat gat aac act gtt att att ggc tct gcc aac ata       2793
Leu Leu Ile Ala Asp Asp Asn Thr Val Ile Ile Gly Ser Ala Asn Ile
        900                 905                 910 aat gac cgc agc atg ctg gga aag cgt gac agt gaa atg gct gtc att       2841
Asn Asp Arg Ser Met Leu Gly Lys Arg Asp Ser Glu Met Ala Val Ile
915                 920                 925                 930 gtg caa gat aca gag act gtt cct tca gta atg gat gga aaa gag tac       2889
Val Gln Asp Thr Glu Thr Val Pro Ser Val Met Asp Gly Lys Glu Tyr
                935                 940                 945 caa gct ggc cgg ttt gcc cga gga ctt cgg cta cag tgc ttt agg tct       2937
Gln Ala Gly Arg Phe Ala Arg Gly Leu Arg Leu Gln Cys Phe Arg Ser
            950                 955                 960 aaa atg act cca ggt gtc gaa gat ccc tgatctttgg caagaagatg             2984
Lys Met Thr Pro Gly Val Glu Asp Pro
        965                 970 caaattttaa actaatctgt ggtgaagcag agagaatact gggctaggaa gctgggctcg     3044
tttcagctgt gcgatcctaa ataagtccat tcaataaagt gttatttaga actttcaaaa    3104
aaaaaaaaaa                                                           3114

<210> SEQ ID NO 19
<211> LENGTH: 971
<212> TYPE: PRT
<213> ORGANISM: Homo sapiens

<400> SEQUENCE: 19

Met Ser Leu Lys Asn Glu Pro Arg Val Asn Thr Ser Ala Leu Gln Lys
 1               5                  10                  15
```

```
Ile Ala Ala Asp Met Ser Asn Ile Ile Glu Asn Leu Asp Thr Arg Glu
             20                  25                  30
Leu His Phe Glu Gly Glu Val Asp Tyr Asp Val Ser Pro Ser Asp
         35                  40                  45
Pro Lys Ile Gln Glu Val Tyr Ile Pro Phe Ser Ala Ile Tyr Asn Thr
         50                  55                  60
Gln Gly Phe Lys Glu Pro Asn Ile Gln Thr Tyr Leu Ser Gly Cys Pro
 65              70                  75                  80
Ile Lys Ala Gln Val Leu Glu Val Glu Arg Phe Thr Ser Thr Thr Arg
                 85                  90                  95
Val Pro Ser Ile Asn Leu Tyr Thr Ile Glu Leu Thr His Gly Glu Phe
             100                 105                 110
Lys Trp Gln Val Lys Arg Lys Phe Lys His Phe Gln Glu Phe His Arg
         115                 120                 125
Glu Leu Leu Lys Tyr Lys Ala Phe Ile Arg Ile Pro Ile Pro Thr Arg
         130                 135                 140
Arg His Thr Phe Arg Arg Gln Asn Val Arg Glu Glu Pro Arg Glu Met
145                 150                 155                 160
Pro Ser Leu Pro Arg Ser Ser Glu Asn Met Ile Arg Glu Glu Gln Phe
             165                 170                 175
Leu Gly Arg Arg Lys Gln Leu Glu Asp Tyr Leu Thr Lys Ile Leu Lys
         180                 185                 190
Met Pro Met Tyr Arg Asn Tyr His Ala Thr Thr Glu Phe Leu Asp Ile
         195                 200                 205
Ser Gln Leu Ser Phe Ile His Asp Leu Gly Pro Lys Gly Ile Glu Gly
210                 215                 220
Met Ile Met Lys Arg Ser Gly Gly His Arg Ile Pro Gly Leu Asn Cys
225                 230                 235                 240
Cys Gly Gln Gly Arg Ala Cys Tyr Arg Trp Ser Lys Arg Trp Leu Ile
                 245                 250                 255
Val Lys Asp Ser Phe Leu Leu Tyr Met Lys Pro Asp Ser Gly Ala Ile
             260                 265                 270
Ala Phe Val Leu Leu Val Asp Lys Glu Phe Lys Ile Lys Val Gly Lys
         275                 280                 285
Lys Glu Thr Glu Thr Lys Tyr Gly Ile Arg Ile Asp Asn Leu Ser Arg
 290                 295                 300
Thr Leu Ile Leu Lys Cys Asn Ser Tyr Arg His Ala Arg Trp Trp Gly
305                 310                 315                 320
Gly Ala Ile Glu Glu Phe Ile Gln Lys His Gly Thr Asn Phe Leu Lys
                 325                 330                 335
Asp His Arg Phe Gly Ser Tyr Ala Ala Ile Gln Glu Asn Ala Leu Ala
             340                 345                 350
Lys Trp Tyr Val Asn Ala Lys Gly Tyr Phe Glu Asp Val Ala Asn Ala
         355                 360                 365
Met Glu Glu Ala Asn Glu Glu Ile Phe Ile Thr Asp Trp Trp Leu Ser
         370                 375                 380
Pro Glu Ile Phe Leu Lys Arg Pro Val Val Glu Gly Asn Arg Trp Arg
385                 390                 395                 400
Leu Asp Cys Ile Leu Lys Arg Lys Ala Gln Gln Gly Val Arg Ile Phe
                 405                 410                 415
Ile Met Leu Tyr Lys Glu Val Glu Leu Ala Leu Gly Ile Asn Ser Glu
             420                 425                 430
```

```
Tyr Thr Lys Arg Thr Leu Met Arg Leu His Pro Asn Ile Lys Val Met
        435                 440                 445
Arg His Pro Asp His Val Ser Ser Thr Val Tyr Leu Trp Ala His His
    450                 455                 460
Glu Lys Leu Val Ile Ile Asp Gln Ser Val Ala Phe Val Gly Gly Ile
465                 470                 475                 480
Asp Leu Ala Tyr Gly Arg Trp Asp Asp Asn Glu His Arg Leu Thr Asp
            485                 490                 495
Val Gly Ser Val Lys Arg Val Thr Ser Gly Pro Ser Leu Gly Ser Leu
        500                 505                 510
Pro Pro Ala Ala Met Glu Ser Met Glu Ser Leu Arg Leu Lys Asp Lys
        515                 520                 525
Asn Glu Pro Val Gln Asn Leu Pro Ile Gln Lys Ser Ile Asp Asp Val
    530                 535                 540
Asp Ser Lys Leu Lys Gly Ile Gly Lys Pro Arg Lys Phe Ser Lys Phe
545                 550                 555                 560
Ser Leu Tyr Lys Gln Leu His Arg His Leu His Asp Ala Asp Ser
            565                 570                 575
Ile Ser Ser Ile Asp Ser Thr Ser Ser Tyr Phe Asn His Tyr Arg Ser
        580                 585                 590
His His Asn Leu Ile His Gly Leu Lys Pro His Phe Lys Leu Phe His
    595                 600                 605
Pro Ser Ser Glu Ser Glu Gln Gly Leu Thr Arg Pro His Ala Asp Thr
610                 615                 620
Gly Ser Ile Arg Ser Leu Gln Thr Gly Val Gly Glu Leu His Gly Glu
625                 630                 635                 640
Thr Arg Phe Trp His Gly Lys Asp Tyr Cys Asn Phe Val Phe Lys Asp
            645                 650                 655
Trp Val Gln Leu Asp Lys Pro Phe Ala Asp Phe Ile Asp Arg Tyr Ser
        660                 665                 670
Thr Pro Arg Met Pro Trp His Asp Ile Ala Ser Ala Val His Gly Lys
    675                 680                 685
Ala Ala Arg Asp Val Ala Arg His Phe Ile Gln Arg Trp Asn Phe Thr
690                 695                 700
Lys Ile Met Lys Ser Lys Tyr Arg Ser Leu Ser Tyr Pro Phe Leu Leu
705                 710                 715                 720
Pro Lys Ser Gln Thr Thr Ala His Glu Leu Arg Tyr Gln Val Pro Gly
            725                 730                 735
Ser Val His Ala Asn Val Gln Leu Leu Arg Ser Ala Ala Asp Trp Ser
        740                 745                 750
Ala Gly Ile Lys Tyr His Glu Glu Ser Ile His Ala Ala Tyr Val His
    755                 760                 765
Val Ile Glu Asn Ser Arg His Tyr Ile Tyr Ile Glu Asn Gln Phe Phe
770                 775                 780
Ile Ser Cys Ala Asp Asp Lys Val Val Phe Asn Lys Ile Gly Asp Ala
785                 790                 795                 800
Ile Ala Gln Arg Ile Leu Lys Ala His Arg Glu Asn Gln Lys Tyr Arg
            805                 810                 815
Val Tyr Val Val Ile Pro Leu Leu Pro Gly Phe Glu Gly Asp Ile Ser
        820                 825                 830
Thr Gly Gly Gly Asn Ala Leu Gln Ala Ile Met His Phe Asn Tyr Arg
    835                 840                 845
Thr Met Cys Arg Gly Glu Asn Ser Ile Leu Gly Gln Leu Lys Ala Glu
```

```
                850             855             860
Leu Gly Asn Gln Trp Ile Asn Tyr Ile Ser Phe Cys Gly Leu Arg Thr
865             870             875             880

His Ala Glu Leu Glu Gly Asn Leu Val Thr Glu Leu Ile Tyr Val His
                885             890             895

Ser Lys Leu Leu Ile Ala Asp Asp Asn Thr Val Ile Ile Gly Ser Ala
            900             905             910

Asn Ile Asn Asp Arg Ser Met Leu Gly Lys Arg Asp Ser Glu Met Ala
        915             920             925

Val Ile Val Gln Asp Thr Glu Thr Val Pro Ser Val Met Asp Gly Lys
    930             935             940

Glu Tyr Gln Ala Gly Arg Phe Ala Arg Gly Leu Arg Leu Gln Cys Phe
945             950             955             960

Arg Ser Lys Met Thr Pro Gly Val Glu Asp Pro
                965             970
```

<210> SEQ ID NO 20
<211> LENGTH: 24
<212> TYPE: PRT
<213> ORGANISM: castor bean

<400> SEQUENCE: 20

```
Leu Lys Ile Leu Ser Lys Ile Ala Ala Gly Glu Arg Phe Thr Val Tyr
1               5               10              15

Ile Val Val Pro Met Trp Pro Glu
            20
```

<210> SEQ ID NO 21
<211> LENGTH: 24
<212> TYPE: PRT
<213> ORGANISM: dbEST#204986

<400> SEQUENCE: 21

```
Gln Arg Ile Leu Lys Ala His Arg Glu Asn Gln Lys Tyr Arg Val Tyr
1               5               10              15

Val Val Ile Pro Leu Leu Pro Gly
            20
```

<210> SEQ ID NO 22
<211> LENGTH: 24
<212> TYPE: PRT
<213> ORGANISM: yeast

<400> SEQUENCE: 22

```
Asp Arg Ile Val Lys Ala Asn Gln Glu Lys Lys Pro Trp Lys Ala Phe
1               5               10              15

Ile Leu Ile Pro Leu Met Pro Gly
            20
```

<210> SEQ ID NO 23
<211> LENGTH: 24
<212> TYPE: DNA
<213> ORGANISM: oligonucleotide/primer

<400> SEQUENCE: 23
gtccatgcta atgtacagtt gctc                                    24

<210> SEQ ID NO 24
<211> LENGTH: 24
<212> TYPE: DNA

-continued

```
<213> ORGANISM: oligonucleotide/primer

<400> SEQUENCE: 24
ttccctgtga gctttcagga tcct                                          24

<210> SEQ ID NO 25
<211> LENGTH: 20
<212> TYPE: DNA
<213> ORGANISM: oligonucleotide/primer

<400> SEQUENCE: 25
cgccaacgcg aggtgctagc                                               20
```

PHOSPHATIDYLCHOLINE PHOSPHOLIPASE D

CROSS REFERENCE TO RELATED APPLICATIONS

The application is a continuation-in-part (CIP) of U.S. Ser. No. 08/768,147, filed Dec. 17, 1996, now U.S. Patent No. 5,859,222, which claims priority to U.S. Provisional Application Ser. No. 60/008,768, filed Dec. 15, 1995 the contents of which are incorporated herein by reference.

TECHNICAL FIELD OF THE INVENTION

In general, the invention pertains to human polynucleotide sequences encoding for polypeptides having enzymatic activity relevant in cell signaling. The present application pertains in particular to mammalian phosphatidylcholine phospholipase D (PCPLD), specifically, human PCPLD (hPCPLD), to fragments and polypeptide analogs thereof and to polynucleotides encoding the same.

BACKGROUND OF THE INVENTION

Cell activation is associated with rapid upregulation of synthesis of phospholipids (PL) that includes phosphatidic acid (PA), diacylglycerol (DAG) and phosphatidylinositol (PI). PA's are a molecularly diverse group of phospholipid second messengers coupled to cellular activation and mitogenesis. Singer et al., *Exp. Opin. Invest. Drugs* 3:631643, 1994. Compounds capable of modulating PA generation and hence altering a signal involved in cell activation may therefore be of therapeutic interest in the area of inflammation and oncology.

Lysophosphatidic acid acyltransferase (LPAAT) is an important enzyme in the synthesis of a specific species of PA in activated monocytic cells. Rice et al., *Proc. Nat'l Acad. Sci. USA* 91:3857–3861, 1994. PCPLD is another major enzyme class involved in the generation of PA through hydrolysis of phosphatidyl choline (PC) into PA and choline. Exton, *Biochim Biophys Acta* 1212:2642, 1994). Okamura et al., *J. Biol. Chem.* 269:31207–31213, 1994, report PCPLD protein purification from pig lung. Brown et al., *J. Biol. Chem.* 270:14935–14943, 1995, report PCPLD protein purification from porcine brain, and Vinggaard et al. discuss PCPLD isolation from human placenta. *Biochim Biophys Acta* 1258:169–176, 1995.

In plant species, Wang et al. published results of cloning efforts with castor bean PCPLDs. *J. Biol. Chem.* 269:20312–20317, 1994. Ueki et al. disclose PCPLD purified from rice and maize, *Plant Cell Physiol.* 36:903–914, 1995, and there also are reports on PCPLD isolation and purification from yeast. Ella et al., *Biochem. J.* 314, 15–19, 1996; Rose et al., *Proc. Natl. Acad. Sci.* 92: 12151–12155, 1995.

Most recently, Hammond et al. report cloning of a human isoform of PCPLD, hPLD1. *J. Biol. Chem.* 270: 29640–29643, 1995. SEQ ID NO. 3 is a sequence listing of the amino acids of hPLD1. Based on a variety of biochemical studies including differential subcellular fractionation, distinct mechanism of activation, substrate specificity and different chromatographic properties, evidence for the existence of multiple phospholipase D (PLD) isoforms in mammalian cells is growing rapidly. Liscovitch et al., *Chem. Phys. Lipids* 80: 37–44, 1996; Kiss, *Chem. Phys. Lipids* 80: 81–102. hPLD1 has approximately a 40% sequence homology with hPCPLD.

Although other mammalian PLD sequences have been cloned, heretofore the sequence of the disclosed PCPLD has not been obtained. Therefore, cloning cDNA isoforms of PLD that are closely related to other mammalian and plant isoforms of PLD would be useful in conducting discovery research to identify specific agents capable of modulating this enzyme.

SUMMARY OF THE INVENTION

This present invention relates to three, previously unknown isoforms, hPCPLD2.1, hPCPLD2.2, and hPCPLD1.5, which are hereafter called "hPLD2.1," "hPLD2.2" and "HPLD1.5," respectively. Thus, the invention provides cDNA sequences, polypeptide sequences, and transformed cells for producing isolated, recombinant hPLD2. 1, hPLD2.2 or hPLD1.5. The invention conternplates, inter alia, the incorporation of codons "preferred" for expression by selected nomnammalian hosts, the provision of sites for cleavage by restriction endonuclease enzymes, and the provision of initial, terminal or intermediate DNA sequences which facilitate construction of readily expressed vectors.

The invention also provides DNA sequences coding for microbial expression of polypeptide analogs or derivatives of bPLD2.1, hPLD2.2 or hPLD1.5, which differ from naturally-occurring forms, in terms of the identity or location of one or more amino acid residues, and which share some or all properties of naturally occurring forms. Accordingly, the invention encompasses deletion analogs that contain fewer than all of the residues specified for hPLD2. 1, hPCD 2.2, or hPLD1.5; substitution analogs, such as [Ser$^{17}$]PLD, where one or more amino acid residues are added to a terminal or medial portion of the polypeptide.

As described in greater detail below, hPLD2.1 and hPLD2.2 polypeptides display PCPLD activity in a particular fluorescent assay. Accordingly, the present invention includes polynucleotide sequences that are useful for expressing, in procaryotic or eucaryotic host cells, polypeptide products that have at least a primary structure and a biological property in common with naturally-occurring hPLD2. 1 or hPLD2.2.

With the aforementioned assay, the present inventors have not observed activity associated with hPLD1.5, under circumstances where hPLD2.1 and hPLD2.2 were active in the assay (see below). Because hPLD1 and hPLDI.5 share substantial aspects of primary structure, however, hPLD1.5 may display PCPLD activity under other circumstances. In any event, the present invention encompasses assays for screening test compounds for their ability to inhibit hPLD2.1 or hPLD2.2. Accordingly, hPLD1.5 protein can be used as a negative control in the context of screening compounds for inhibition of PCPLD1 activity, pursuant to the present invention. Also, a polynucleotide encoding hPLD1.5 can be used as a probe to identify genes encoding other PCPLD isoforms.

More generally, the present invention contemplates a category of polynucleotides that __includes, without limitation, (a) an isolated DNA that encodes hPLD2.1, hPLD2.2 or hPLD1.5; (b) a DNA that hybridizes, under conditions such as are illustrated herein or are more stringent conditions, to a DNA set forth in this specification or to a fragment thereof; (c) a DNA that, but for the degeneracy of the genetic code, would hybridize to DNA sequences disclosed herein; and (d) an antisense oligonucleotide for modulating expression of hPLD2. 1, hPLD2.2 or hPLD1.5. Subcategory (b) includes, without limitation, genomic DNA sequences encoding allelic variants of hPLD2.1, hPLD2.2 or hPLD1.5. Subcategory (c) includes, without limitation, manufactured DNAs encoding hPLD2.1, hPLD2.2 or hPLD1.5, fragments of these proteins, and analogs of the proteins, which DNAs optionally incorporate codons facilitating translation messenger RNA in a prescribed microbial or other host.

To these ends, the present invention provides, in accordance with one of its aspects, a polynucleotide (i) that codes for a PCPLD isoform selected from group consisting of hPLD2. 1, hPLD2.2, and hPLD1.5 or (ii) that hybridizes to a polynucleotide encoding said isoform. In a preferred embodiment, the polynucleotide comprises the nucleotide sequence of SEQ ID NOS. 1 & 2, 16 & 17 or 18 & 19, respectively.

In accordance with another aspect of the present invention, an isolated PCPLD isoform is provided, selected from a group consisting of hPLD2. 1, hDLD2.2, and hPLD1.5. Pursuant to one preferred embodiment, the isolated PCPLD isoform comprises the amino acid sequence of SEQ ID NOS. 1 & 2 and of SEQ ID NO. 16 & 17, or an enzymatically active fragment thereof. According to another embodiment, the isolated PCPLD isoform comprises the amino acid sequence of SEQ ID NOS. 18 & 19.

In accordance with yet another aspect of the present invention, a method is provided for screening a drug candidate, comprising (a) providing at least one of the aforementioned isoforms that displays PCPLD activity, (b) contacting that isoform with the drug candidate, and then (c) determining whether the drug candidate affects PCPLD activity of the isoform.

In a preferred embodiment, step (c) comprises measuring the PCPLD activity of the isoform against a control sample, which can contain a PCPLD isoform comprising the amino acid sequence of SEQ ID NOS. 18 & 19. In another embodiment, the drug candidate is a pool of compounds from combinatorial library expression.

BRIEF DESCRIPTION OF THE DRAWINGS

As shown in FIG. 3, an increase in the concentration of CT-2584 correlates to an increase in fluorescent intensity of the products corresponding to NBD-Pa-Bt, NBD-LPA-Bt, and NBD-PA bands on the TLC plate.

DETAILED DESCRIPTION OF PREFERRED EMBODIMENTS

Figure 1:
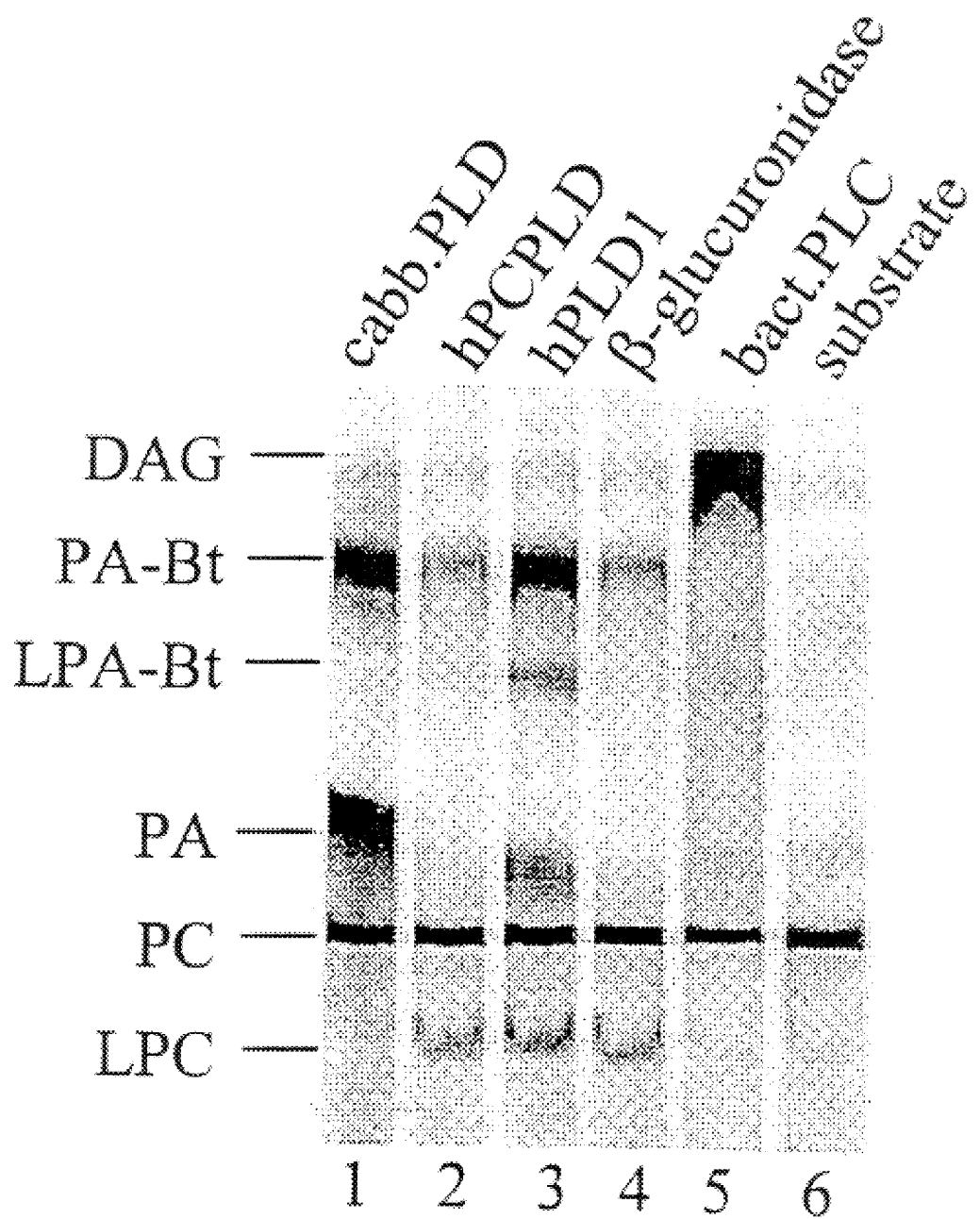
FIG. 1 shows TLC analysis of PCPLD activity in Sf9 cell extracts transfected with various Baculoviral constructs expressing hPLD2. 1, also referred to as hPCPLD, and hPLD1 by using a fluorescent-labeled PC substrate.

In the description that follows, a number of terms are utilized extensively. Definitions are provided to facilitate understanding of the invention.

Definitions

The term "isolated" applied to a polypeptide throughout the specification refers to the purity of the polypeptide that is sufficiently free of other materials endogenous to the host, from which the polypeptide is isolated, such that any remaining materials do not materially affect the biological properties of the polypeptide. The term "derived" as used throughout the specification in relation to a polypeptide of the invention, encompasses (a) a polypeptide obtained by isolation or purification from host cells, as well as a polypeptide obtained by manipulation and expression of a polynucleotide prepared from host cells; (b) a polynucleotide including genomic DNA, MRNA, cDNA synthesized from MRNA, and a synthetic oligonucleotide having a sequence corresponding to an inventive polynucleotide; and (c) a synthetic polypeptide antigen prepared based on any known polypeptide sequence of the invention.

The term "expression product" as used throughout the specification refers to materials produced by recombinant DNA techniques.

PCPLD catalyzes the hydrolysis of phospholipids to PA. The preferred substrate for this reaction is PC, a major mammalian cell-membrane constituent. Recombinant hPCPLD is useful in screening drug candidates which inhibit or activate hPCPLD activity. The invention provides (a) a polynucleotide, which encodes a polypeptide, comprising a DNA sequence set forth in SEQ ID NO. 1 (hPLD2.1), NO. 16 (hPLD2.2) or NO. 18 (hPLD1.5); (b) a shortened polynucleotide thereof, or an additional polynucleotide, which due to the degeneracy of the genetic code encodes a polypeptide of SEQ ID NO. 1, NO. 17 or NO. 19, or a biologically active fragment thereof; (c) a polynucleotide capable of hybridizing thereto; and (d) a polypeptide which comprises a polypeptide sequence of SEQ ID NO. 1, NO. 15 or NO. 16, or a biologically active fent thereof.

The invention also provides a vector containing a DNA sequence encoding hPLD2.1, hPLD2.2, or HPLD1.5 in operative association with an expression control sequence, and a host cell transformed with such a vector to produce recombinant hPLD2.1, hPLD2.2, or hPLD1.5. An inventive vector and a transformed cell are employed in a process to produce recombinant hPLD2.1, hPLD2.2, or hPLD1.5. In this process, a cell line transformed with a DNA sequence encoding hPLD2.1, hPLD2.2, or HPLD1.5 in operative association with an expression control sequence, is cultured. The process may employ a number of known cells as host cells for the expression of hPLD2.1, hPLD2.2, or hPLD1.5, including, for example, mammalian cells, yeast cells, insect cells and bacterial cells.

The invention further includes a method to select a pharmaceutically active compound by determining whether the compound is capable of inhibiting the enzymatic activity of hPLD2.1, hPLD2.2, hPLD 1.5. A selected compound could be a pharmaceutical drug useful to inhibit a signal cascade in an inflammatory response.

The invention further provides a transformed cell that expresses active hPLD2.1 or hPLD2.2, and further comprises a means for determining whether a drug candidate is therapeutically active by inhibiting or activating the enzymatic activity of a recombinant PCPLD.

Accordingly, hPLD2.1 is characterized by the 933 amino acids of SEQ ID NOS. 1 & 2; hPLD2.2 is characterized by the 933 amino acids of SEQ ID NOS. 16 & 17; and hPLD1.5 is characterized by the 971 amino acids of SEQ ID NOS. 18 & 19. The invention includes an allelic variant (naturally-occuinng base changes in the species which may or may not result in an amino acid change) of a DNA sequence herein encoding hPLD2.1, hPLD2.2, or hPLD1.5 polypeptide, or an active fragment thereof. The inventive polynucleotide sequences further comprise a sequence which hybridizes under stringent conditions to the coding region (e.g., nucleotide #66 to nucleotide #2864). Regarding hybridization conditions, see Maniatis et al., MOLECULAR CLONING: A LABORATORY MANUAL, Cold Spring Harbor Laboratory, pages 387–389, 1982. For example, one such stringent hybridization condition is 4×SSC at 65° C., followed by a wash in 0.1×SSC at 65° C. for 30 minutes. Another stringent hybridization condition is 50% formamide and 4×SSC at 42° C.

The present invention further includes a polynucleotide encoding an enzymatic active polypeptide whose codon is the same as hPLD2.1 or hPLD2.2, or differs due to the degeneracy of genetic code. In addition, the invention encompasses a variant with a point mutation or an induced modification of a polynucleotide sequence set forth in SEQ ID NOS. 1 & 2, NOS. 16 & 17, or NOS. 18 & 19, which enhances the enzymatic activity or the production of the encoded polypeptide.

Identification of Coding Sequences

A search of the Genbank with the blastp program, using the castor bean PCPLD protein sequence as a probe, disclosed a yeast DNA sequence (Genbank Accession # Z28256) that encodes a *S. cerevisiae* reading frame (ORF YKRO3 1c) mapped to chromosome XI. This sequence contains several short stretches of amino acids homologous to the plant PCPLD protein sequence. Recently, this yeast sequence has been identified to encode the SPO14 gene (Genbank Accession# L46807), which is essential for yeast meiosis. Honigberg et al., *Genetics* 130:703–716, 1992. The gene product for SPO14 has been recently found to contain PCPLD activity. Ella, et al., *Biochem. J.* 314, 15–19, 1996; Rose, et al., *Proc. Nat'l Acad. Sci.* 92: 12151–12155, 1995. This yeast protein sequence was then used to search for homologous sequences in the Genbank database of expressed sequence tag (dbEST). Translated polypeptide sequence of several short stretches of human cDNA sequences were found homologous to the plant PCPLD and the yeast SPO14 protein sequence. These cDNA sequences of interest were derived from single-run partial sequencing of random human cDNA clones carried out by either the WashU-Merck EST or the Genexpress-Genethon program.

1. hPLD2

(A) hPLD2.1

An example of a short stretch of amino acid sequence homology alignment among the plant, yeast and two overlapping human cDNA clones (Genbank #R83570 and dbEST #261972) is shown, wherein castor bean PCPLD fragment is SEQ ID NO:4, yeast is SEQ ID NO:5, and R83570 is SEQ ID NO 6.

5'-GTCATCTGCGATGAGCACCTTGCTGTG-3' (o.R83570. IR) (SEQ ID NO: 8), were synthesized (Life Technologies, Gaithersburg, Md.) based on the putative coding sequence corresponding to nucleotides 44–67 and complement sequence corresponding to nucleotides 168–194 of the human cDNA clone genbank#R83570, respectively.

o.R83570.1 was used in combination with the primer 5'-CTAGCTTATAATACGACTCA C-3' (o.sport.1R) (SEQ ID NO. 9) corresponding to the vector sequence just downstream of the cDNA cloning region of the plasmid pCMV.SPORT (Life Technologies, Gaithersburg, Md.) to isolate the 3'-region of the human PCPLD cDNA from a human lung cDNA library (Life Technologies, Gaithersburg, Md.) using Expand™ long template PCR (Boehringer Mannheim, Indianapolis, Ind.). The PCR fragments generated were cleaved with Nco I and Xho I prior to subcloning into the Litmus28 vector (New England Biolab, Beverly, Mass.). DNA sequence analysis showed that cDNA clone pL28.NX has a 1,200 bp Nco I-Xho I insert, a polyA tail at one end and an open reading frame with several stretches homologous to amino acids 766–862, 1228–1275 and 1338–1360 of SPO14, suggesting that this clone contained the C-terminal coding region of human PCPLD and its 3'-untranslated region.

o.R83570.1R was used in combination with the primer 5'-GACTCTAGCC TAGGCTTG C-3' (o.sport. 1) (SEQ ID NO: 10) corresponding to the vector sequence just upstream of the cDNA cloning region of the plasmid pCMV.SPORT (Life Technologies, Gaithersburg, Md.) to isolate the 5'-region of the human PCPLD cDNA from a human lung cDNA library (Life Technologies, Gaithersburg, Md.) using Expandm long template PCR (Boehringer Mannheim, Indianapolis, Ind.). The PCR fragments generated were either cleaved with Sst I and Asp718 I or with Sst I alone prior to subcloning into the pBluescriptKS(-) vector (Stratagene, LaJolla, Calif.). DNA sequence analysis displayed that the cDNA clone pKS.Sst has a 1,190 bp Sst I—Sst I insert and an open reading frame homologous to amino acids 401–780 of SPO14, indicating that this clone contained the central coding region of human PCPLD.

To isolate the 5'-region of the human PCPLD CDNA, a synthetic oligonucleotide 5'-CTCAGGACTCAACCACCAGT C-3' (o.pld3.2R, SEQ ID NO 11) was designed (Life Technologies, Gaithersburg, Md.) based on the complement sequence corresponding to the region about 50 bp downstream of the Sst I site on the 5'-side of the 1190 bp Sst I fragment. o.pld3.2R was used in

| Castor bean PCPLD | Q | R | S | M | D | G | A | R | D | S | E | I | A | M | G | A | Y | Q | P |
| Yeast SPO14 | | E | R | S | Q | L | G | N | R | D | S | E | V | A | I | L | I | R | D | T |
| R83570/261972 | | D | R | S | L | L | G | K | R | D | S | E | L | A | V | L | I | E | D | T |

The top row refers to the partial protein sequence of the castor bean PCPLD from amino acid 679 to 698; the middle row refers to the partial protein sequence of the yeast SPO14 from amino acid 813 to 831; and the bottom row refers to a homologous protein sequence derived from human cDNA clone genbank #R83570 and dbEST #261972. Identical amino acids sequences among these three sequences are shown in bold letters.

Accordingly, syntheticoligonucleotides5 '-GTATTCAATCCTGCATCGCCTTAA-3' (o.R83570.1) (SEQ ID NO: 7) and combination with the primer 5'-GACTCTAGCC TAG-GCTTTTG C-3' (o.sport. 1) corresponding to the vector sequence just upstream of the cDNA cloning region of the plasmid pCMV.SPORT (Life Technologies, Gaithersburg, Md.) to isolate the 5'-region of the human PCPLD cDNA from a human lung cDNA library (Life Technologies, Gaithersburg, Md.) using ExpandT™ long template PCR (Boehringer Mannheim, Indianapolis, Ind.). The PCR fragments generated were cleaved with EcoR I prior to subcloning into the pBluescript(II)SK(-) vector (Stratagene, LaJolla, Calif.) between the EcoR I site and Sma I site. DNA sequence analysis disclosed that cDNA clone pSK.R83.16 has a 1,240 bp insert containing an ATG near the 5'-end and an open reading frame with several major stretches homologous to amino acids 1–10, 153–262, and 328410 of SPO14, implying that this cDNA clone contained the N-terminal coding region of human PCPLD. It has recently been reported that SPO14 protein has PCPLD activity (Engebrecht et al., ASBMB Fall Symposium, 1995), again suggesting that a human sequence with extensive homology to the yeast SPO14 protein probably has PCPLD activity.

To assemble the human PCPLD cDNA clone, the following fragments were isolated:

1) The 1197 bp Hind III-Sst I fragment from pSK.R83.16.
2) The 512 bp Sst I-Sfu I fragment from pKS.Sst. 3) The 660 bp Sfu I-Ban I fragment from pKS.Sst. 4) The 1129 bp Ban I-Xho I fragment from pL28.NX.

Fragments 1 and 2 were inserted via a three-part ligation into pLitmus28 (New England Biolab, Beverly, Mass.) cleaved with Sfu' I and Hind II to generate pL28.HS. Fragments 3 and 4 were inserted via a three-part ligation into pLitmus28 cleaved with Sfu I and Xho I to generate pL28.SX. The 1700 bp Hind III-Sfu I fragment, derived from pL28.HS and the 1780 bp Sfu I-NotI fragment, derived from pL28.SX, were then inserted via a three-part ligation into the expression vector pCE2, cleaved with Hind III and NotI to generate pCE2.PLD. pCE2.PLD is transfected into various mammalian cells to assay for PCPLD activity using labeled-PC as a substrate. Ella et al., *Anal. Biochem.* 218: 136–142, 1994.

The plasmid pCE2 was derived from pREP7b (Leung et al., Proc. Nat'l Acad. Sci. USA, 92:48134817, 1995) with the RSV promoter region replaced by the CMV enhancer and the elongation factor-1a (EF-1a) promoter and intron. The CMV enhancer came from a 380 bp Xba I-Sph I fragment produced by PCR from pCEP4 (Invitrogen, San Diego, Calif.) using primers 5'-GGCTCTAGATATTAATAGTAATCAATTAC-3' (SEQ ID NO. 12) and 5'-CCTCACGCATGCACCATGGTAATAGC-3' (SEQ ID NO 13). The EF-1a promoter and intron (Uetsuki et al., *J. Biol. Chem.*, 264: 5791–5798, 1989) came from a 1200 bp Sph I-Asp718 I fragment produced by PCR from human genomic DNA using the primers 5'-GGTGCATGCGTGAGGCTCCGGTGC-3' (SEQ ID NO. 14) and 5'-GTAGTTTTCACGGTACCTGAAATGGAAG-3' (SEQ ID NO. 15). These two fragments were ligated into a Xba I/Asp718 I digested vector derived from pREP7b to generate pCE2 Nucleotide sequencing analysis of various human PCPLD cDNA inserts was -performed. SEQ ID NOS. 1 & 2 shows the DNA sequence of the cDNA insert of the hPLD2.1 isolated herein and the predicted amino acids sequence using the first ATG (nucleotide positions 66–68) from the 5'-end of the sequence for the start of translation. This open reading frame encodes a 933 amino acid polypeptide (SEQ ID NOS. 1 & 2) and followed by a 3'-untranslated region of >550 bp. Although the putative initiation site for translation at nucleotide positions 66–68 fulfilled the requirement for an adequate initiation site (Kozak, *Critical Rev. Biochem. Mol. Biol.* 27:385402, 1992), translation may still start further upstream of the sequence shown here, as there is no in frame stop codon preceding the 933 amino acid shown here.

The sequence of the 933 amino acid open reading frame in pCE2.PLD was used as the query sequence to search for homologous sequences in protein databases. Search of the database based on Genbank Release 91 from the National Center for Biotechnology Information (NCBI) using the blastp program showed that the protein encoded by pCE2.PLD was homologous to the yeast SP014 and the various plant PCPLDs.

(B) hPLD2.2

Three overlapping hPLD2.2 cDNA fragments were isolated from a human liver cDNA library (Life Technologies, Gaithersburg, Md.) using the hPLD2.1 cDNA fragment as a probe. For the assembly of a full-leng hPLD2.2 cDNA clone, the 1,600 bp EcoRI-BstBI fragment, the 660 bp BstBI-BanI fragment, and the 1,145 bp BanI-NotI fragment were ligated into the EcoRI-NotI vector of pBluescriptSK (Stratagene, La Jolla, Calif.) to generate plasmid pSK.PLD2.2. DNA sequence analysis showed that the sequence of hPLD2.2 (SEQ ID NOS. 16 & 17) was identical to that of hPLD2.1 (SEQ ID NOS. 1 & 2) with the exceptions of 8 nucleotide changes scattered throughout the entire molecule.

| Nucleotide acids | | Amino acids | |
|---|---|---|---|
| position | change | position | change |
| 660 | A–C | 184 | Glu–Asp |
| 718 | T–C | 504 | Ser–Pro |
| 1296 | A–G | 404 | Lys–Arg |
| 1614 | T–G | 502 | Asn–Lys |
| 2154 | G–C | 682 | Lys–Asn |
| 2372 | A–G | 755 | Asp–Gly |
| 2524 | A–G | 806 | Ser–Gly |
| 2840 | A–T | 911 | Lys–Met |

2. hPLD1.5

Another example of alignment of short stretch of amino acid sequences from plant PLD, yeast PLD and a human cDNA clone (dbEST#204986) is shown, wherein castor bean PLD fragment is SEQ ID NO: 20, dbEST#204986 is SEQ ID NO: 21, and yeast PLD is SEQ ID NO: 22:

Castor bean PLD LKILSKIAAGERFTVYWVPMWPE
dbEST# 204986 QRILKAHREN(KYRVYVVIPLLPG
Yeast PLD DRIVKANQEKPWKAFILIPLMPG The top row refers to the castor bean PCPLD sequence (Wang, et al., *J. Biol. Chem.* 269: 20312–20317, 1994) of amino acids 551–574, the middle row refers to homologous translated sequence derived from a human cDNA clone dbEST#204986, and the bottom row refers to the yeast PCPLD sequence of amino acids 1002–1025. Identical amino acids among these three sequences are doubly underlined, whereas conservative amino acids are singly underlined.

Accordingly, an oligonucleotides 5'-GTCCATGCTA ATGTACAGTT GCTC-3' (o. 204986.1) (SEQ ID NO: 23), was synthesized (Life Technologies, Gaithersberg, Md.) based on the putative coding sequence of the human cDNA clone dbEST#204986, in which one nucleotide was changed from C to T to generate a BsrG I site. o.204986.1 was used in combination with o.sport. IR to isolate the 3'-region of the human PCPLD cDNA from a human liver cDNA library (Life Technologies, Gaithersburg, Md.) using Expand™ long template PCR (Boehringer Mannheim, Indianapolis, Ind.). Two PCR fragments, 1,300 bp and 900 bp, were generated. These two fragments were cleaved with BsrG I and Xho I prior to subcloning into the Litmus28 vector between the Acc65 I and the Xho I site. DNA sequence analysis showed that the open reading frame of the cDNA clone pL28.Li.29 with the 1,300 bp insert matched perfectly with amino acids 742–1074 of HPLD1 sequence (Hammond, et al., *J. Biol. Chem.* 270: 29640–29643, 1995), whereas the cDNA clone pL28.Li.8 with the 900 bp insert contained a divergent coding sequence after amino acid 961 of hPLD1 and only the first 650 bp of the insert matched with hPLD1 DNA sequence, suggesting that pL28.Li.8 represented an alternatively spliced variant of hPLD1 encoding a protein with a different C-terminal sequence.

To isolate the 5'-region of the human PCPLD cDNA from a human liver cDNA library (Life Technologies, Gaithersburg, Md.) using ExpandT™ long template PCR (Boehringer Mannheimn, Indianapolis, Ind.), a primer 5'-TTCCCTGTGA GCTTTCAGGA TCCT-3' (o.pld1.R) (SEQ ID NO: 24) complementary to the region corresponding to amino acids 804–810 of hPLD1 was used in combination with the primer 5'-CGCCAACGC GAGGTGCTAG C-3' (o.pld1.1F) (SEQ ID NO: 25) corresponding to the region near the Nhe I site in the 5'-untranslated region of hPLD1. The PCR fragments generated were cleaved with Nhe I and BamH I. The fragments of about 2,400 bp were isolated from agarose gel prior to subcloning into the pLitmus38 vector (New England Biolab, Beverly, Mass.). DNA sequence analysis showed that cDNA clone pL38.1.6 with a 2,450 bp Nhe I-BamH I insert contained an open reading frame with perfect match to amino acids 1–805 of hPLD1

To assemble the various hPLD1 isoforms, the following two fragments were isolated:

1) The 2,500 bp BsrG I-BamH I fragment from pL38.1.6.
2) The 662 bp BamH I-Not I fragment from pL28.Li.8.

Fragments 1 and 2 were inserted via a three-part ligation into pBluescriptSK(−)II cleaved with Acc65 I and Not I to generate pskPLD1.5.

Nucleotide sequencing of hPLD1.5 insert was performed. (SEQ ID NO. 18 & 19) shows that the DNA sequence and amino acid sequence of hPLD1.5. The first 961 amino acids of the 971 amino acids of hPLD1.55 is identical to the first 961 amino acids of hPLD1 (SEQ ID NO: 3).

Peptide Sequencing of Polypeptides

Purified polypeptides prepared by the methods described above can be sequenced using methods well known in the art, for example using a gas phase peptide sequencer (Applied Biosystems, Foster City, Calif.). Because the proteins of the present invention may be glycosylated, it is preferred that the carbohydrate groups are removed from the proteins prior to sequencing. This can be achieved by using glycosidase enzymes. Preferably, glycosidase F (Boehringer-Mannheim, Indianapolis, Ind.) is used. To determine as much of the polypeptide sequence as possible, it is preferred that the polypeptides of the present invention be cleaved into smaller fragments more suitable for gas-phase sequence analysis. This can be achieved by treatment of the polypeptides with selective peptidases, and in a particularly preferred embodiment, with endoproteinase lys-C (Boehringer). The fragments so produced can be separated by reversed-phase HPLC chromatography.

Production of Polypeptides

Once the entire coding sequence of a gene is determined, the DNA sequence of the gene can be inserted into an appropriate expression system. Gene expression can be achieved in any number of different recombinant DNA expression systems to generate large amount of such polypeptide. The present invention includes a polypeptide with a native glycosylation sequence, or a deglycosylated or unglycosylated polypeptide prepared by the methods described below. Expression systems known to the skilled practitioner in the art include bacteria such as *E. coli*, yeast such as *Pichia pastoris*, baculovirus, and mammalian expression systems such as Cos or CHO cells. In a preferred embodiment, a recombinant protein is expressed in *E. coli* or baculovirus expression system. A complete gene or, alternatively, fragments of the gene encoding an antigenic determinant can be expressed. In a first preferred embodiment, the DNA sequence encoding the polypeptide is analyzed to detect putative transmembrane sequences. Such sequences are typically very hydrophobic and readily detected by using standard sequence analysis software, such as MacDNASIS (Hitachi, San Bruno, Calif.). The presence of transmembrane sequences is often deleterious when a recombinant protein is synthesized in many expression systems, especially *E. coli*, as it leads to insoluble aggregates which are difficult to be renatured into a native conformation of the polypeptide. Deletion of taansmembrane sequences normally does not significantly alter the conformation of the remaining polypeptide structure. Moreover, a transmembrane sequence, by definition embedded within a membrane, is inaccessible as an antigenic determinant to a host immune system. Antibodies to such a sequence will not, therefore, provide immunity to the host and, hence, little information is lost in terms of immunity by omitting such a sequence from a recombinant polypeptide of the invention. Deletion of a transmembrane-encoding sequence from a gene used for expression can be achieved by standard techniques. See Ausubel et al., supra, Chapter 8. For example, fortuitously-placed restriction enzyme sites can be used to excise the desired gene fragment, or the PCR can be used to amplify only the desired part of the gene.

Alternatively, computer sequence analysis is used to determine the location of the predicted major antigenic determinant epitopes of a recombinant polypeptide. Software capable of carrying out this analysis is readily available commercially, for example MacDNASIS (Hitachi, San Bruno, Calif.). The software typically uses standard algorithms such as the Kyte/Doolittle or Hopp/Woods methods to locate hydrophilic sequences which are characteristically found on the surface of polypeptides and are, therefore, likely to act as antigenic determinants. Once this analysis is completed, a polypeptide can be prepared to contain at least the essential features of an antigenic determinant. A polynucleotide encoding such a determinant can be constructed and inserted into an expression vector by a standard method, for example, using PCR cloning methodology. Polypeptide sequence variants can be substitutional, insertional or deletion variants. Deletion variants lack one or more residues of the native polypeptide which are not essential for PCPLD activity, and are exemplified by the variants lacking a transmembrane sequence described above. Another common type of deletion variant is one lacking a secretory signal sequence or a signal sequence directing a polypeptide to bind a particular part of a cell.

A substitutional variant typically contains an exchange of one amino acid for another at one or more sites within the polypeptide, and is designed to modulate one or more properties of the polypeptide such as stability against proteolytic cleavage. A substitution is preferably conservative, that is, one amino acid is replaced with one of similar shape and charge. A conservative substitution is well known in the art and includes, for example, changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. An insertional variant could be a fusion protein used for rapid purification of a polypeptide, a hybrid polypeptide containing a sequence of another protein, or a polypeptide which is homologous to an inventive polypeptide. For example, an insertional variant could contain a portion of the amino acid sequence of the polypeptide from one species, together with a portion of the homologous polypeptide from another species. An insertional variant could also be one with additional amino acids introduced within the coding sequence. Such an insertion is typically smaller than a fusion protein described above and is introduced, for example, to disrupt a protease cleavage site.

A gene or gene fragment encoding a desired polypeptide can be inserted into an expression vector by standard subcloning techniques. In a preferred embodiment, an *E. coli* expression vector is used to produce a recombinant protein as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6×His system (Qiagen, Chatsworth, Calif.). Some of these systems produce recombinant polypeptides bearing only a small number of additional amino acids, which are unlikely to affect the LPAAT ability of the recombinant polypeptide. For example, both the FLAG system and the 6×His system add only short sequences. The two systems are known to be poorly antigenic and do not adversely affect folding of the polypeptide to its native conformation. Other fusion systems produce a protein where it is desirable to excise the fusion partner from the desired protein. In a preferred embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.) or enterokinase. LaVallie e al., *J. Biol. Chem.* 268:23311–17, 1993.

In another preferred embodiment, the expression system used is one driven by the baculovirus polyhedron promoter. A gene encoding a polypeptide can be manipulated by standard techniques in order to facilitate cloning into the baculovirus vector. See Ausubel et al., supra. A preferred baculovirus vector is the pBlueBac vector (Invitrogen, Sorrento, Calif.). A vector carrying polynucleotide encoding a polypeptide is transfected into *Spodoptera frugiperda* (Sf9) cells by standard protocols, and the cells are cultured and processed to produce a recombinant polypeptide. See Summers et aL, A MANUAL FOR METHODS OF BACULOVIRUS VECTORS AND INSECT CELL CULTURE PROCEDURES, Texas Agricultural Experimental Station.

Purification of Polypeptides

In accordance with the invention, a protein is isolated from host cells, and tested for their ability to produce a desired biological response. Polypeptide extracts can be prepared from host cells by standard methods known to the art. See, for example, Harlow and Lane, *Antibodies, A Laboratory Manual*, Cold Spring Harbor Press, 1987 and *Current Protocols in Molecular Biology*, John Wiley & Sons 1995. In a preferred embodiment, host cells are extracted into a buffer, and the extracts are separated into membrane and soluble fractions. Each fraction is tested for biological activity. Fractions which elicit a desired biological activity are then purified further to determine which components are responsible for the activity. At each step of the purification, fractions can be assayed for enzymatic activity by the means described above. Purification of the active fractions can be carried out by methods known to the art. See, for example, *Protein Purification Methods—A Practical Approach*, Harris et al., Eds. (IRL Press, Oxford, 1989).

In a preferred embodiment, extracts prepared as above are purified by sequential size exclusion chromatography isoelectric focusing, HPLC size exclusion chromatography, and chromatography on an affinity column. Fractions which display PCPLD activity can be analyzed further by SDS-PAGE analysis to determine the approximate molecular mass of the active component. It is known that many naturally occurring polypeptides are glycosylated to varying degrees and, as a consequence, a single protein often appears as a pattern of bands of differing electrophoretic mobility on SDS-PAGE analysis. In such situations, it can be difficult to determine whether such a pattern is due to heterogeneity in glycosylation of a single amino acid chain or due to the presence of contaminating polypeptides. To distinguish between these two situations, the polypeptide fraction under study can be treated with a glycosidase to remove some or all the carbohydrate moieties from the protein. The SDS-PAGE analysis is repeated under both reducing and non-reducing conditions, and the resulting banding patterns compared. If the electrophoretic bands observed on the gel show similar or identical shifts in mobility after enzyme treatment, this is an indication that the electrophoretic heterogeneity observed in the purified protein fraction is due to variations in glycosylation. Conversely, if the electrophoretic mobilities differ significantly, it is evident that contaminated polypeptides are present. In a preferred embodiment of the invention, the glycosidase is glycosidase F (Boehringer-Mannheim, Indianapolis, IN) and the peptidase is endoproteinase glu-C (Boehringer). A polypeptide may also be treated with a peptidase to be cleaved into fragments for reversed phase HPLC mapping.

Some polypeptides have previously been purified from host cells and it is important therefore to exclude the possibility that biological activity in a particular fraction is due to the presence of these polypeptides. The presence of known polypeptides in a mixture can be detected by methods well known to the art, for instance, by Western blotting with an antiserum specific for the known polypeptide. In a preferred embodiment of the invention, previously identified polypeptides are removed from fractions containing antigenic activity by passage over affinity columns prepared using antibodies or antiserum specific for the known polypeptides.

A polypeptide expressed in any of a number of different recombinant DNA expression systems can be obtained in large amounts and tested for biological activity. Recombinant bacterial cells, for example *E. coli*, are grown in any of a number of suitable media, for example LB, and the expression of a recombinant polypeptide is induced by adding IPTG to the media or switching incubation to a higher temperature. After culturing the bacteria for a furer period of between 2 and 24 hours, the cells are collected by centrifugation and washed to remove residual media. The bacterial cells are then lysed, for example, by disruption in a cell homogenizer and centrifuged to separate the dense inclusion bodies and cell membranes from the soluble cell components. The centrifugation can be performed under conditions whereby the dense inclusion bodies are selectively enriched by incorporation of sugars such as sucrose into the buffer and centrifugation at a selective speed. If a recombinant polypeptide is expressed in the inclusion, these can be washed in any of several solutions to remove some of the contaminating host proteins, then solubilized in solutions with high concentration of urea (e.g., 8 M) or chaotropic agents such as guanidine hydrochloride in the presence of reducing agents such as B-mercaptoethanol or DTT (dithiothreitol).

At this stage it may be advantageous to incubate the polypeptide for several hours under conditions suitable for the polypeptide to undergo a refolding process into a conformation which more closely resembles that of the native polypeptide. Such conditions generally include a polypeptide at a concentration less than 500 mg/ml, a reducing agent at low concentration, urea of less than 2 M and often reagents, such as a mixture of reduced and oxidized glutathione which facilitate the interchange of disulfide bonds within the protein molecule. The refolding process can be monitored, for example, by SDS-PAGE or with antibodies which are specific for the native molecule. Following refolding, the polypeptide can then be purified further and separated from the refolding mixture by chromatography with ion exchange resins, or gel permeation resins, or by a variety of affinity columns.

More specifically, an oligonucleotide and a polynucleotide encoding a polypeptide of the invention can be used as hybridization probes, capable of recognizing and specifically binding to a complementary polynucleotide nucleotide sequence, providing thereby a means of detecting, identifying, locating and measuring a complementary polynucleotide sequence in a biological sample.

Biological samples include, among a great many others, blood or blood serum, lymph, ascites fluid, urine, microorganism or tissue culture medium, cell extracts, or the like, derived from a biological source, or a solution containing chemically synthesized protein, or an extract or solution prepared from such biological-sourced fluid. It is further intended to include cells, tissue and other organic matter such as feces, food and plants.

An oligonucleotide containing a modified nucleotide of the invention can be used as a primer to initiate nucleic acid synthesis at locations in a DNA or RNA molecule comprising the sequence complementary to an inventive oligonucleotide sequence (SEQ ID NOS. 1 & 2, NOS. 16 & 17, or NOS. 18 & 19). The synthesized polynucleotide would have incorporated, at its 5' terminus, the oligonucleotide primer bearing an inventive sequence and would, therefore, be detectable by exploitation of the characteristics of a detectable label. Two such primers, specific for different nucleotide sequences on complementary strands of dsDNA, can be used in the polymerase chain reaction (PCR) to synthesize and amplify a polynucleotide. A detectable label present on a primer will facilitate the identification of desired PCR products. PCR, combined with techniques for preparing complementary DNA (cDNA) can be used to amplify various RNAs, with oligonucleotide primers to provide points for initiation of synthesis in the cDNA duplex flanking the desired sequence and to identify a desired product. Primers labeled with the invention may also be utilized for enzymatic nucleic acid sequencing by the dideoxy chain-termination technique.

Alternatively, expression vectors are introduced into Brassica tissues using a direct gene transfer method such as microprojectile-mediated delivery, DNA injection, electroporation, and the like. See, for example, Gruber et al., supra; Miki et al., supra; Klein et al., Biotechnology 10:268, 1992.

PCR Backgound Information

Polymerase chain reaction (PCR) technology is employed in a growing variety of ways, including preparation of cDNAs and constructing cDNA libraries. An early use of PCR to generate a cDNA library was reported by Belyavsky et al., *Nucleic Acids Res.* 17:2919–32, 1989. The Belyavsky method utilized oligo (dT) as a primer for reverse transcriptase reaction, followed by poly (dG) tailing via the action of terminal deoxynucleotidyl transferase (Td-f). The resulting dG-tailed cDNAs were subsequently amplified with poly (dT) and poly (dC) primers. The cDNA pool obtained was cloned into a vector for subsequent cDNA screening. Since an oligo (dI) primer can anneal at any position of the poly(A) tail of a (+) strand of cDNA, and an oligo (dC) primer can anneal at any position of the poly(G) tail of a (−) strand of cDNA, the amplified cDNAs generated by the Belyavsky method often have varying lengths. Accordingly, these products cannot be analyzed directly, and instead require subcloning and screening of a cDNA library, a time-consuming technique. Furthermore, the use of primers containing homopolymers on the 3' end typically yields a high background of non-specific product.

A technique for rapid amplification of cDNA ends (RACE) was in Frohman et al., *Proc. Nat'l. Acad. Sci. USA* 85:8998–9002, 1988, and Frohman, *PCR Protocols, A Guide to Methods and Applications*, 28–38 (Academic Press 1990). The RACE protocol produces specific cDNAs by using PCR to amplify the region between a single point on a transcript and the 3' or the 5' ends. One requires knowledge of the sequence of an internal portion of the transcript, however, in order to design a primer for use in conjunction with either the polyT or polyG primers to amplify the ends. This protocol yields specific cDNAs products only, not whole libraries.

A modification to the RACE protocol introduced by Borson et al., *PCR Methods and Applications* 2:14448, 1992, entails the use of a "lock-docking oligo (dT)." The locking mechanism involves extending the poly dT primer, by either one nucleotide (A, C or G) or by two nucleotides (also A, C or G) and yet one more of the four possible nucleotides, at the 3'-end of the primer. This "locks" the primer to the beginning of the poly dT tail, either the natural dT or a poly dT tail attached to the first strand cDNA 3'-end, by use of TdT, resulting in the synthesis of cDNA's of discrete lengths. Subcloning and screening of subclone library is not necessary before analysis, which can speed up the inquiry. Like the RACE protocol, however, Borson's protocol uses a gene-specific internal primer and, hence, produces only specific cDNAs, not whole libraries.

Approaches are described in the literature to identify MRNA expressed differentially, either in only some cell types, or at certain times of a biological process, or during infection by a parasite or a virus, etc. Those studies generally employ subtractive hybridization to reveal the differentially expressed mRNA(s). Liang and colleagues have used the anchored-end technique to look for specific differences in MRNA populations. Liang et al., *Nucleic Acids Res.* 21:3269–75, 1993. The Liang method, called "differential display," employs a decanucleotide of arbitrary sequence as a primer for PCR, internal to the MRNA, and a polyTMN primer on the 3'-end of mRNAs; "M" in this context is randomly G, C or A, but N is chosen as one of the four possible nucleotides. When such sets of primers are employed, patterns of mRNAs can be visualized, upon polyacrylamide gel electrophoresis of the PCR product, and the comparison of such patterns produced by mRNAs from two sources reveal the differentially expressed mRNAs.

The differential display method can indicate the individual, differently expressed mRNA's, but cannot constitute a complete library of such mRNA's. As a furter consequence of having one primer of an arbitrary sequence, and therefore probably not having an exact match, low copy number mRNAs may not be picked up by this method.

Finally, the cDNA candidates identified would still require recovery from the gel and subcloning, if the individual cDNA is desired for further analysis.

Lisitsyn et al., Science 259:946–51, 1993, have described a representational differences analysis (RDA) which uses subtractive hybridization and PCR technology to define the differences between two genomes. Like other subtractive hybridization protocols, in RDA there are defined two sets of DNAs, the "tester" DNA and the "driver" DNA. According to the RDA protocol, the DNA of the two genomes to be compared are digested by restriction endonucleases, and a dephoshorylated double-stranded oligonucleotide adapter is ligated. After denaturation and hybridization of driver and tester DNA, oligonucleotides from the adapters covalently linked to tester DNA were used to amplify unique DNA sequences of tester library. The adapters are partially double-stranded DNAs made by partially complementary oligos, where the single-stranded sequence at one end of the double stranded adapter is complementary to the single-strand tail of the digested genomic DNA. The combined use of (i) restriction enzyme, digested DNA as PCR substrate and (ii) the preferential amplification of shorter substrates results in a population of fairly short, amplified DNA molecules. The adapters then are removed by cleavage with the restriction enzymes used originally to digest the DNA. To the tester DNA, new adapters with novel sequences are ligated, the tester and driver DNA are mixed, the DNA strands are separated by heating ("melting"), and the DNA's are cooled to allow for reannealing. PCR is performed with primers complementary to the adapters on tester DNA, thereby amplifying only target DNA, i.e., only DNA unique to the tester DNA. By restriction enzyme digestion of the adapters from the amplified DNA and ligation of additional, novel adapters, followed by PCR, the target DNA is amplified to become the dominant fraction.

The RDA procedure does not use any physical method of separation between the tester and driver DNA which, if used, would allow enhanced purification of target DNA. The method is used only to identify differences between genomes and was not used to identify differential cDNA expression.

Expression vectors that are suitable for production of PCPLD polypeptide typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. PCPLD polypeptide of the present invention preferably is expressed in eukaryotic cells, such as mammalian, insect and yeast cells. Mammalian cells are especially preferred eukaryotic hosts because mammalian cells provide suitable post-translational modifications such as glycosylation. Examples of mammalian host cells include Chinese hamster ovary cells (CHO-K1; ATCC CCL61), rat pituitary cells (GH$_1$; ATCC CCL82), HeLa S3 cells (ATCC CCL2.2), rat hepatoma cells (H-4-II-E; ATCC CRL1548) SV40-transformed monkey kidney cells (COS-1; ATCC CRL 1650) and murine embryonic cells (NIH-3T3; ATCC CRL 1658). For a mammalia host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273,1982); the TK promoter of Herpes virus (McKnight, *Cell* 31: 355, 1982); the SV40 early promoter (Benoist et al., *Nature* 290:304, 1981); the Rous sarcoma virus promoter (Gorman et al., *Proc. Nat'l. Acad. Sci. USA* 79:6777, 1982); and the cytomegalovirus promoter (Foecking et al., Gene 45:101, 1980). Alternatively, a prokaryotic promoter, such as the bacteriophage T3 RNA polymerase promoter, can be used to control fusion gene expression if the prokaryotic promoter is regulated by a eukaryotic promoter. Zhou et al., *Mol. Cell. Biol.* 10:4529, 1990; Kaufmnan et al., *Nucl. Acids Res.* 19:4485, 1991.

An expression vector can be introduced into host cells using a variety of techniques including calcium phosphate transfection, liposome-mediated transfection, electroporation, and the like. Preferably, transfected cells are selected and propagated wherein the expression vector is stably integrated in the host cell genome to produce stable transformants. Techniques for introducing vectors into eukaryotic cells and techniques for selecting stable transformants using a dominant selectable marker are described, for example, by Ausubel and by Murray (ed.), *Gene Transfer and Expression Protocols* (Humana Press 1991).

DNA molecules encoding the human PCPLD gene can be used to detect the level of PCPLD gene expression in tissue samples. Such a detection method can be used, for example, to compare the amount of PCPLD RNA in a sample obtained from normal tissue and in a sample isolated from methotrexate-resistant tumor tissue. The presence of relatively low levels of PCPLD RNA in the tumor sample would indicate that methotrexate resistance is due, at least in part, to underexpression of the PCPLD gene. This result also would indicate that treatment of a mammal having such a tumor with methotrexate should be augmented by PCPLD gene therapy.

In testing a tissue sample for PCPLD RNA using a nucleic acid hybridization assay, RNA can be isolated from tissue by sectioning on a cryostat and lysing the sections with a detergent such as SDS and a chelating agent such as EDTA, optionally with overnight digestion with proteinase K. Such tissue is obtained by biopsy. A preferred quantity of tissue is in the range of 1–10 milligrams. Protein is removed by phenol and chloroform extractions, and nucleic acids are precipitated with ethanol. RNA is isolated by chromatography on an oligo dT column and then eluted from the column. Further fractionation also can be carried out according to methods well known to those of ordinary skill in the art.

A number of techniques for molecular hybridization are used for the detection of DNA or RNA sequences in tissues. When large amounts of tissue are available, analysis of hybridization kinetics provides the opportunity to accurately quantitate the amount of DNA or RNA present, as well as to distinguish sequences that are closely related but not identical to the probe. Reactions are run under conditions of hybridization (Tm-25° C.) in which the rate of reassociation of the probe is optimal. Wetmur et al., *J. Mol. Biol.* 31:349, 1968. The kinetics of the reaction are second order when the sequences in the tissue are identical to those of the probe; however, the reaction exhibits complex kinetics when probe sequences have partial homology to those in the tissue. Sharp et al., *J. Mol. Biol.* 86:709, 1974.

The concentration of probe to cellular RNA is determined by the sensitivity desired. To detect one transcript per cell would require about 100 pg of probe per mg of total cellular DNA or RNA. The nucleic acids are mixed, denatured, brought to the appropriate salt concentration and temperature, and allowed to hybridize for various periods of time. The rate of reassociation can be determined by quantitating the amount of probe hybridized either by hydroxyapatite chromatography (Britten et al., Science 161:529, 1968) or by S1 nuclease digestion (Sutton, Biochim. Biophys. Acta 240:522, 1971).

A more flexible method of hybridization is the northern blot technique. The particular hybridization technique is not essential to the invention, and any technique commonly used in the art being within the scope of the present invention. Typical probe technology is described in U.S. Pat. No. 4,358,535 to Falkow et al., incorporated by reference herein. For example, hybridization can be carried out in a solution containing 6×SSC (10×SSC: 1.5 M sodium chloride, 0.15 M sodium citrate, pH 7.0), 5×Denhardt's (1×Denhardt's: 0.2% bovine serum albumin, 0.2% polyvinylpyrrolidone, 0.02% Ficoll 400), 10 mM EDTA, 0.5% SDS and about 10' cpm of nick-translated DNA for 16 hours at 65 ° C.

The hybridization assays of the present invention are particularly well suited for preparation and commercialization in kit form, the kit comprising a carrier means compartmentalized to receive one or more container means (vial, test tube, etc.) in close confinement, with each container means comprising one of the separate elements to be used in hybridization assay. For example, there may be a container means containing PCPLD DNA molecules suitable for labeling by "nick translation," or containing labeled PCPLD DNA or labeled PCPLD RNA molecules. Further container means may contain standard solutions for nick translation of DNA comprising DNA polymerase I/DNase I and unlabeled deoxyribonucleotides.

Antibodies to human PCPLD protein can be obtained using the product of an PCPLD expression vector as an antigen. The preparation of polyclonal antibodies is well-known to those of skill in the art. See, for example, Green et al., "Production of Polyclonal Antisera," in Immmunochemical Protocols (Manson, ed.), pages 1–5 (Humana Press 1992). Alternatively, PCPLD antibody of the present invention may be derived from a rodent monoclonal antibody (MAb). Rodent monoclonal antibodies to specific antigens may be obtained by methods known to those skilled in the art. See, for example, Kohler and Milstein, Nature 256:495, 1975, and Coligan et al. (eds.), Current Protocols in Immunology, 1:2.5.1–2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1–2.7.12 and pages 2.9.1–2.9.3. Also, see Baines et al., "Purification of Tmmiunoglobulin G (IgG)," in Methods in Molecular Biology, 10:79–104 Humana Press, Inc. 1992. A PCPLD antibody of the present invention may also be derived from a subhuman primate antibody. General techniques for raising therapeutically useful antibodies in baboons may be found, for example, in Goldenberg et al., international patent publication No. WO 91/11465 (1991), and in Losman et al., Int. J. Cancer 46:310, 1990.

Alternatively, a therapeutically useful PCPLD antibody may be derived from a "humanized" monoclonal antibody. Humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., Proc. Nat'l. Acad. Sci. USA 86:3833, 1989. Techniques for producing humanized MAbs are described, for example, by Jones et al., Nature 321:522, 1986, Riechmann et al., Nature 332:323, 1988, Verhoeyen et al., Science 239:1534, 1988, Carter et al., Proc. Nat'l Acad. Sci. USA 89:4285, 1992, Sandhu, Crit. Rev. Biotech. 12: 437, 1992, and Singer et al., J. Immun. 150:2844, 1993, each of which is hereby incorporated by reference.

As an alternative, a PCPLD antibody of the present invention may be derived from human antibody fragments isolated from a combinatorial immunoglobulin library. See, for example, Barbas et al., METHODS: A Companion to Methods in Enymology 2:119 1991, and Winter et al., Ann. Rev. Immunol. 12:433, 1994, which are incorporated by reference. Cloning and expression vectors that are useful for producing a human immunoglobulin phage library can be obtained, for example, from STRATAGENE Cloning Systems (La Jolla, Calif.). In addition, a PCPLD antibody of the present invention may be derived from a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13, 1994; Lonberg et al., Nature 368:856, 1994, and Taylor et al., Int. Imnnnm. 6:579, 1994.

The invention, illustrated by the following examples, should not be deemed as limited in any way by the following representative examples.

Example 1

Figure 3:
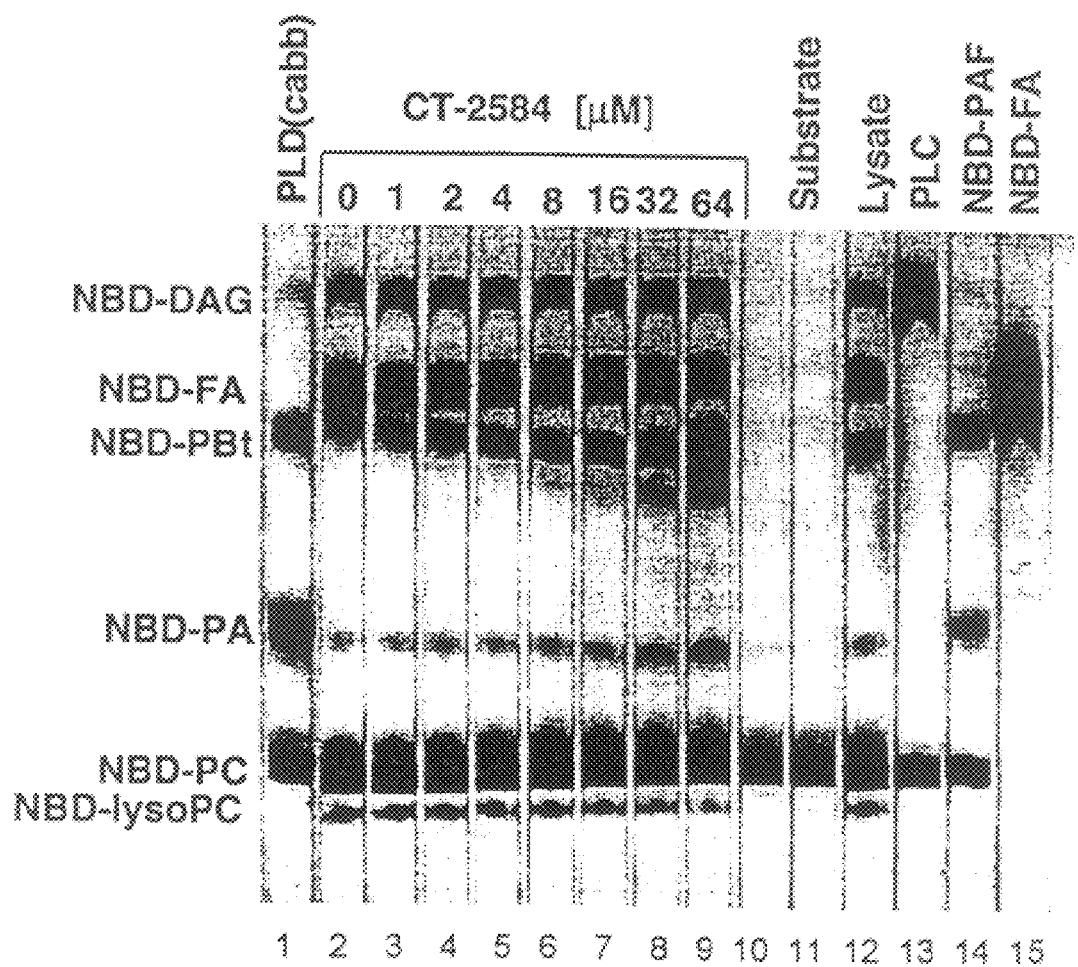
FIG. 3 displays the effect of CT-2584 on PCPLD activity in insect cell extracts transfected with a Baculoviral construct expressing hPID1.

This example illustrates that the recombinant human PCPLD enzymes are useful in developing a screening assay for compounds that modulate PCPLD activity. FIGS. 1 and 3 show two examples of a screening assay for PCPLD activity in cell extracts based on a fluorecent asssay (Ella, et al., Anal. Biochem. 218: 136–142, 1994) with the major exception that, instead of using the substrate BPC (Molecular Probes, Eugene, Oreg.), we used a synthetic phosphatidylcholine (PC) substrate with a fluorescent NBD moiety incorporated into the end of the acyl-chain at the SN1 position of PC (NBD-PC). BPC contains an ether linkage at the sn-1 position, while NBD-PC contains an acyl linkage at the sn-1 position. Having an acyl linkage at the sn1 position provides the additional opportunity to examine PLA1 activity along with other PC-hydrolysing phospholipases such as PCPLD, PCPLC, and PLA2 at the same time.

The assay for PCPLD uses the transphosphatidylation (Saito, et al., *Arch. Biochem. Biophys.* 169: 318–323, 1975) reaction as a means of definig PCPLD activity. This reaction occurs when PCPLD hydrolyses PC into PA and choline in presence of a primary alcohol, such as butanol, where PA will be converted to phosphatidylbutanol (PBt). PBt is more resistant to hydrolysis by enzymes such as PA phosphohydrolase (PAPh) and can be easily separated from PC and other products by thin layer chromatography.

Figure 2:
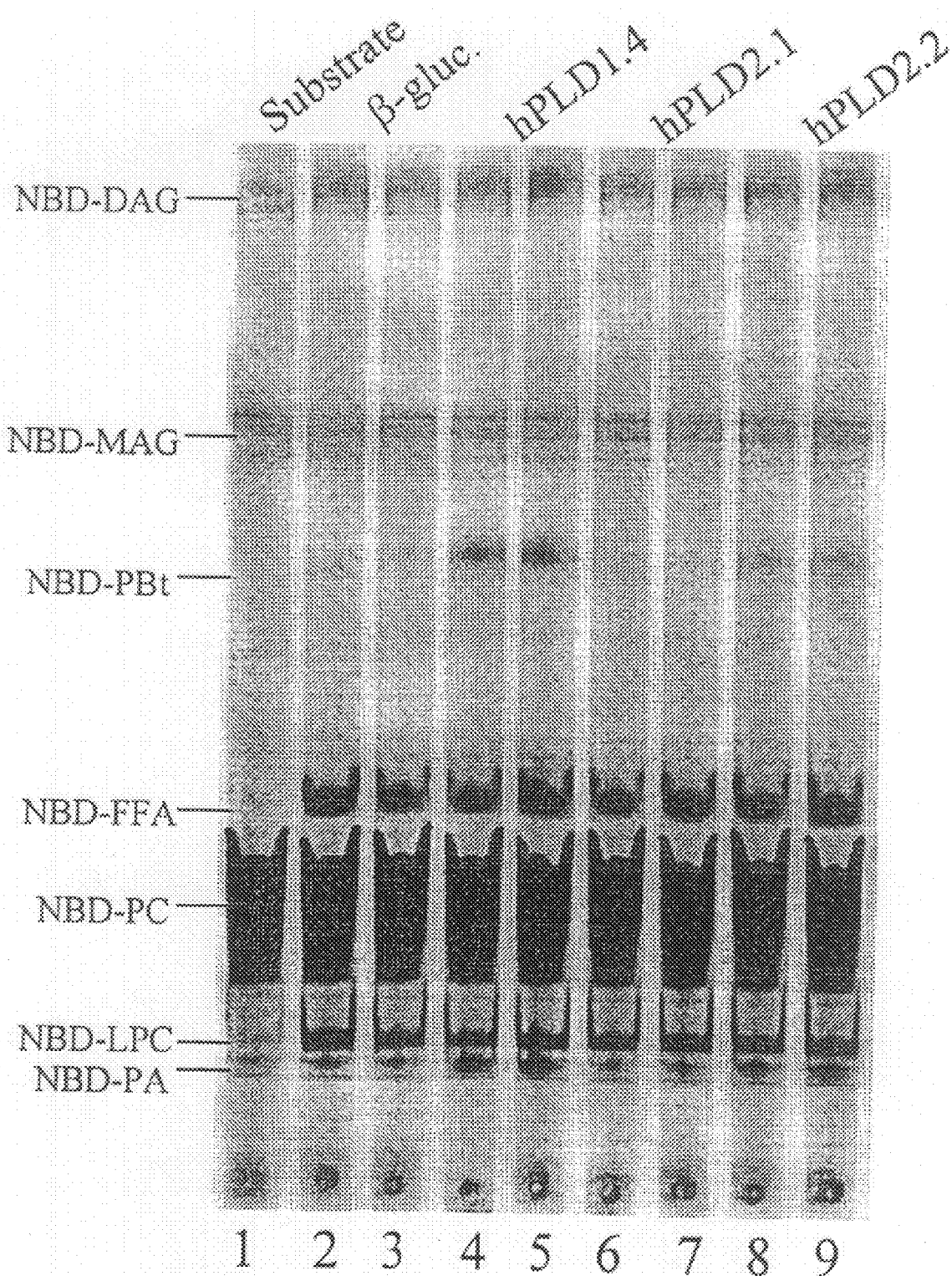
FIG. 2 demonstrates a screening assay for PCPLD activity in Sf9 cell extracts transfected with various Baculoviral constructs expressing hPLD2.2, hPLD2.1 and a human isoform of PLD1, hPLD1β (Hammond et al., *J. Biol. Chem.* 272: 3860–3868, 1997), designated as hPLD1.4 here, using a fluorescent-labeled PC substrate.

In FIGS. 1 and 2, cell lysate was prepared from Sf9 cells transfected with Baculoviral constructs expressing different PCPLD enzymes. The samples were then incubated with NBD-PC for 30 min at 30° before loading onto TLC plates.

FIG. 1 shows the activity level of Sf9 cells transfected with HPLD1 (Hammond, et al., *J. Biol. Chem.* 270: 29640–29643, 1995) and hPLD2. 1, also referred as HPCPLD, as evidenced by the fluorescent intensity of the products corresponding to NBD-PBt and NBD-PA on the TLC plate. LIne I refers to NBD-PC digested with cabbage PCPLD (Sigma, St. Louis, Mo.) for the generation of certain lipid standards. Lanes 2 to 4 refer to NBD-PC treated with cell lysates transfected with Baculoviral constructs expressing hPCPLD, hPLD1, and β-glucuronidase as a negative control. Lane 5 refers to NBD-PC treated with *B. cereus* PCPLC (Sigma, St. Louis, Mo.) for the generation of NBD-DAG standard. Lane 6 refers to the starting substrate, NBD-PC, by itself.

FIG. 2 demonstrates the PCPLD activity in cell extracts transfected with hPLD2. 1, and its isoform, hPLD2.2. Lane 1 refers to the starting substrate, NBD-PC, by itself. Lanes 2 and 3 refer to duplicate samples of NBD-PC treated with cell lysates transfected with Baculoviral constructs expressing -glucuronidase as a negative control. Lanes 4 and 5 refer to duplicate samples of NBD-PC treated with cell lysates transfected with Baculoviral constructs expressing hPLD1.4. Lanes 6 and 7 refer to duplicate samples of NBD-PC treated with cell lysates transfected with Baculoviral constructs expressing hPLD2. 1. Lanes 8 and 9 refer to duplicate samples of NBD-PC treated with cell lysates transfected with Baculoviral constructs expressing hPLD2.2. The result displays that Sf9 cells transfected with HPLD1.4, hPLD2. 1, or hPLD2.2 contain approximately 12-fold, 1.5-fold, and 4-fold, respectively, higher activities of PCPLD, as evidenced by the increased fluorescent intensity of the products corresponding to NBD-PBt and NBD-PA on the TLC plate (lanes 4 to 9) when compared to controls (lanes 2 and 3). hPLD2.2 was found to have higher PCPLD activity than hPLD2. 1, suggesting that some of the minor changes in amino acid sequence can affect the enzymatic activity.

Example 2

This example illustrates how recombinant HPLD1, as representative of other PLD isoforms, could be used in a screening assay for compounds that modulate PCPLD activity. The results of this assay are shown in FIG. 3.

FIG. 3 illustrates an example of CT-2584 on recombinant HPLD1 activity. In this particular example, cell lysate was prepared from insect cell extracts transfected with Baculoviral vector expressing hPLD1. The samples were incubated with NBD-PC and butanol along with various concentrations of an anti-tumor compound, CT-2584 for 30 min before loading onto TLC plates (Lanes 3 to 9). Lane 10 refers to NBD-PC, a PC with a NBD-group at the SN1 acyl chain treated with cabbage PLD. Lanes 3 to 9 refer to cell extract treated with various concentrations of CT-2584. Lanes 10 and 11 refer to NBD-PC substrate with no enzyme treatment. Lanes 2 and 12 refer to NBD-PC treated with SF9 lysate overexpressing HPLD1. Lane 13 refers to NBD-PC treated with *B. cereus* PCPLC (Sigma, St. Louis, Mo.) for the generation of NBD-DAG standard. Lane 14 refers to NBD-PAF treated with hPLD1 and lane 15 refers to the mobility of the marker NBD-FA. FIG. 3 shows that increasing concentration of CT-2584 led to increased activity of PCPLD and PCPLC, as evidenced by the increased flourescent intensity of the products corresponding to NBD-Pa-Bt, NBD-LPA-Bt, and NBD-PA on the TLC plate. On the other hand, CT-2584 has little effect on PLA1 and PLA2 activity, as evidenced by the even flourescent intensity of the products corresponding to NBD-free fatty acid (NBD-FFA) and NBD-lysophosphatidic acid (NBD-LPC) across the TLC plate. This tpe of assays is useful to screen for agonists and antagonists of PCPLD, as PCPLD has been found to be activated in response to treatment of cells with various hormones and growth factors (Exton, *Biochim Biophys Acta* 1212: 26–42, 1994).

We claim:

1. An isolated polynucleotide of SEQ ID NO: 16 (i) that codes for a human isoform of phosphatidylcholine phospholipase D, or (ii) that hybridizes under stringent conditions to a polynucleotide of SEQ ID NO: 16 encoding said isoform.

2. A vector comprising the polynucleotide of claim 1.

3. A host cell comprising the polynucleotide of claim 1.

4. A method for producing a phosphatidylcholine phospholipase D isoform, comprising translating the polynucleotide of claim 1 under the conditions that said isoform is expressed in detectable or recoverable amounts.

5. A polynucleotide according to claim 1, comprising nucleotides 64–2862 of SEQ ID NO: 16.

6. An isolated and purified nucleic acid sequence coding an expression for a an enzymatically active human phosphatidylchloline phospholipase D enzyme selected from the group consisting of:

(a) a DNA sequence set forth in SEQ ID NO: 16 and enzymatically active fragments thereof;

(b) a cDNA sequence which, due to the degeneracy of the genetic code, encodes a polypeptide of SEQ ID NO: 17 and enzymatically active fragments thereof; and (c) a cDNA sequence capable of hybridizing under high stringency conditions to a cDNA sequence encoding a polypeptide having phosphatidylchloline phospholipase D enzymatic activity.

7. A vector comprising the polynucleotide of claim 6.

8. A host cell comprising the polynucleotide of claim 6.

9. A method for producing a phosphatidylcholine phospholipase D isoform, comprising translating the polynucleotide of claim 6 under the conditions that said isoform is expressed in detectable or recoverable amounts.

10. A polynucleotide according to claim 6, comprising nucleotides 64–2862 of SEQ ID NO: 16.

* * * * *